US012685489B2

(12) United States Patent
Zhang et al.

(10) Patent No.: US 12,685,489 B2
(45) Date of Patent: Jul. 21, 2026

(54) METHODS AND SYSTEMS FOR DETECTING ECG ANOMALIES

(71) Applicant: Arizona Board of Regents on Behalf of the University of Arizona, Tucson, AZ (US)

(72) Inventors: Chicheng Zhang, Tucson, AZ (US); Christopher Gniady, Tucson, AZ (US); Dharma R. Kc, Tucson, AZ (US); Parth Sandeep Agarwal, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 452 days.

(21) Appl. No.: 18/250,048

(22) PCT Filed: Oct. 22, 2021

(86) PCT No.: PCT/US2021/056167
§ 371 (c)(1),
(2) Date: Apr. 21, 2023

(87) PCT Pub. No.: WO2022/087349
PCT Pub. Date: Apr. 28, 2022

(65) Prior Publication Data
US 2023/0397889 A1 Dec. 14, 2023

Related U.S. Application Data

(60) Provisional application No. 63/104,880, filed on Oct. 23, 2020.

(51) Int. Cl.
*A61B 5/00* (2006.01)
*A61B 5/346* (2021.01)

(52) U.S. Cl.
CPC ............ *A61B 5/7267* (2013.01); *A61B 5/346* (2021.01)

(58) Field of Classification Search
CPC ..... A61B 5/7267; A61B 5/346; A61B 5/7275; A61B 2576/00
See application file for complete search history.

(56) References Cited

U.S. PATENT DOCUMENTS

| | | | |
|---|---|---|---|
| 10,769,528 B1 * | 9/2020 | Wang ..................... | G06N 3/084 |
| 2008/0175451 A1 * | 7/2008 | Hoge ................. | G01R 33/5611 |
| | | | 382/128 |

(Continued)

FOREIGN PATENT DOCUMENTS

WO 2020109630 A1 6/2020

OTHER PUBLICATIONS

Ahmad, Farida B., et al., "The leading causes of death in the us for 2020," JAMA, 325(18):1829-1830, 2021.

(Continued)

*Primary Examiner* — Brian T Gedeon
(74) *Attorney, Agent, or Firm* — Perkins Coie

(57) ABSTRACT

Methods, apparatus and systems for robust and accurate detection of anomalies in medical images and electrocardiograms are disclosed. One example system for training a neural network engine includes a processor that is configured to receive a set of training electrocardiogram signals. At least one electrocardiogram signal in the set of training electrocardiogram signals is associated with metadata identifying a region of interest that includes a heart anomaly. The processor is configured to input the set of training electrocardiogram signals into the neural network engine. The neural network engine is trained using an objective function having a first regularization parameter and a second regularization parameter. The processor is also configured to (Continued)

1300 receiving an input image having a feature of interest
1310 inputting the input image into a neural network model
1320 identifying the feature of interest in the input image by classifying the input image using the neural network model
1330 operate the neural network engine to identify the heart anomaly by classifying the set of training electrocardiogram signals and adjust the neural network engine based on the identified heart anomaly and the metadata.

5 Claims, 20 Drawing Sheets

(56) References Cited

U.S. PATENT DOCUMENTS

| | | | | |
|---|---|---|---|---|
| 2010/0111396 | A1 | 5/2010 | Boucheron | |
| 2017/0360377 | A1 | 12/2017 | Rossi et al. | |
| 2019/0150794 | A1 | 5/2019 | Vrudhula et al. | |
| 2020/0034667 | A1* | 1/2020 | Chen | G06T 5/60 |
| 2020/0214618 | A1 | 7/2020 | Vullings | |
| 2022/0036178 | A1* | 2/2022 | Dimitriadis | G06N 3/098 |

OTHER PUBLICATIONS

Baloglu, Ulas Baran, et al., "Classification of myocardial infarction with multi-lead ecg signals and deep cnn," Pattern Recognition Letters, 122:23-30, 2019.

Dasgupta, Sanjoy, et al., "Learning from discriminative feature feedback," In NeurIPS, pp. 3959-3967, 2018.

Donahue, Jeff, et al., "Annotator rationales for visual recognition,". International Conference on Computer Vision, pp. 1395-1402. IEEE, 2011.

Drew, Barbara J. et al., "Finding ecg readers in clinical practice: is it time to change the paradigm?" Journal of the American College of Cardiology, 64(5):528-528, 2014.

Faramand, Ziad, et al., "Lack of significant coronary history and ecg misinterpretation are the strongest predictors of undertriage in prehospital chest pain," Journal of Emergency Nursing, 45(2):161-168, 2019.

Haq, Amin Ul, et al., "A hybrid intelligent system framework for the prediction of heart disease using machine learning algorithms," Mobile Information Systems, 2018.

HeartFlow. Misdiagnosis is a top concern of cardiac patients.

Hoffmann, Javier, et al., "A survey on machine learning approaches to ecg processing," Signal Processing: Algorithms, Architectures, Arrangements, and Applications (SPA), pp. 36-41. IEEE, 2020.

Hughes, J Weston, et al., "Using multitask learning to improve 12-lead electrocardiogram classification," arXiv preprint arXiv:1812.00497, 2018.

International Search Report and Written Opinion mailed Jan. 26, 2022 for International Patent Application No. PCT/US2021/056167.

Kachuee, Mohammad, et al., "Ecg heartbeat classification: A deep transferable representation," IEEE International Conference on Healthcare Informatics (ICHI), pp. 443-444. IEEE, 2018.

Kay, Edmund, et al., "DropConnected Neural Networks Trained on Time-Frequency and Inter-Beat Features for Classifying Hear Sounds," University of Cambridge, 2017.

Kc, Dharma, et al., "Improving the trustworthiness of image classification models by utilizing bounding-box annotations," 1st NeurIPS workshop on Interpretable Inductive Biases and Physically Structured Learning, 2020.

Lancellotti, Patrizio, et al., "Cancer and cardiovascular mortality risk: is the die cast?" European Heart Journal, 42(1):110-112, 2021.

Luo, Chengsi,et al., "Multi-label classification of abnormalities in 12-lead ecg using 1d cnn and lstm," Machine Learning & Medical Engineering for Cardiovascular Health & Intravascular Imaging & Computer Assisted Stenting, pp. 55-63, 2019.

Mitsuhara, Masahiro, et al., "Embedding human knowledge in deep neural network via attention map," arXiv preprint arXiv:1905.03540, 5, 2019.

Mostayed, Ahmed, et al., "Classification of 12-lead ecg signals with bi-directional lstm network," arXiv preprint arXiv:1811.02090, 2018.

Mousavi, Sajad, et al., "Han-ecg: An interpretable atrial fibrillation detection model using hierarchical attention networks," Computers in biology and medicine, 127:104057, 2020.

Paszke, Adam, et al., "Pytorch: An imperative style, high-performance deep learning library," Advances in neural information processing systems, 32:8026-8037, 2019.

Poulis, Stefanos, et al., "Learning with feature feedback: from theory to practice," In Artificial Intelligence and Statistics, pp. 1104-1113. PMLR, 2017.

Reasat, Tahsin, et al., "Detection of inferior myocardial infarction using shallow convolutional neural networks," IEEE Region 10 Humanitarian Technology Conference, (R10-HTC), pp. 718-721. IEEE, 2017.

Ribeiro, Antonio H., et al., "Automatic diagnosis of the 12-lead ecg using a deep neural network," Nature communications, 11(1):1-9, 2020.

Rieger, Laura, et al., "Interpretations are useful: penalizing explanations to align neural networks with prior knowledge," arXiv preprint arXiv:1909.13584, 2019.

Ross, Andrew Slavin, et al., "Right for the right reasons: Training differentiable models by constraining their explanations," arXiv preprint arXiv:1703.03717, 2017.

Sharma, Manali, et al., "Learning with rationales for document classification," Machine Learning, 107(5):797-824, 2018.

Simonyan, Karen, et al., Deep inside convolutional networks: Visualising image classification models and saliency maps. arXiv preprint arXiv:1312.6034, 2013.

Steijlen, Annemarijn SM, et al., "A novel 12-lead electrocardiogram for home use: development and usability testing," JMIR mHealth and uHealth, 6(7):e10126, 2018.

Strodthoff, Nils et al., Deep learning for ecg analysis: Benchmarks and insights from ptb-xl. arXiv preprint arXiv:2004.13701, 2020.

Tartaglione, Enzo, et al., "Learning Sparse Neural Networks via Sensitivity-Driven Regularization," 32nd Conference on Neural Information Processing Systems, 2018.

Vapnik, Vladimir, et al., "A new learning paradigm: Learning using privileged information," Neural networks, 22(5-6):544-557, 2009.

Velic, Marko, et al., "Computer aided ecg analysis-state of the art and upcoming challenges," In Eurocon 2013, pp. 1778-1784. IEEE, 2013.

Wagner, Patrick, et al., "Ptb-xl, a large publicly available electrocardiogramataset," Scientific data, 7(1):1-15, 2020.

Wang, Chunli, et al., "A 12-lead ecg arrhythmia classification method based on 1d densely connected cnn," Machine Learning & Medical Engineering for Cardiovascular Health & Intravascular Imaging & Computer Assisted Stenting, pp. 72-79, 2019.

Yao, Qihang, et al., "Multi-class arrhythmia detection from 12-lead varied-length ecg using attention-based time-incremental convolutional neural network," Information Fusion, 53:174-182, 2020.

Zaidan, Omar F., et al., "Machine learning with annotator rationales to reduce annotation cost," In Proceedings of the NIPS* 2008 workshop on cost sensitive learning, pp. 260-267, 2008.

Zhang, Dongdong, et al., "Interpretable deep learning for automatic diagnosis of 12-lead electrocardiogram," Iscience, 24(4):102373, 2021.

Zhang, Ning, et al., "Part-based r-cnns for fine-grained category detection," European conference on computer vision, pp. 834-849. Springer, 2014.

Zhang, Ye, et al.. "Rationale-augmented convolutional neural networks for text classification," Proc. of the Conference on Empirical Methods in Natural Lang. Processing, Conf. on Empirical Methods in Natural Lang. Proc., vol. 2016, p. 795.

* cited by examiner (Robust Accuracy)

*(Saliency Measure)*

*(Localization Accuracy)* receiving an input image having a feature of interest

1310 inputting the input image into a neural network model

1320 identifying the feature of interest in the input image by classifying the input image using the neural network model

1330

1400

METHODS AND SYSTEMS FOR DETECTING ECG ANOMALIES

CROSS REFERENCE TO RELATED APPLICATIONS

This patent document is a 371 National Phase Application of International Patent Application No. PCT/US2021/056167, filed Oct. 22, 2021, which claims priority to and benefits of U.S. Provisional Application 63/104,880, titled "METHODS AND SYSTEMS FOR DETECTING ECG ANOMALIES," filed on Oct. 23, 2020. The entire disclosure of the aforementioned applications are incorporated by reference as part of the disclosure of this document.

TECHNICAL FIELD

This patent document relates to signal processing using neural networks, in particular, to feedback-based machine learning system for signal classification.

BACKGROUND

Heart disease is the leading cause of death in the US and worldwide for both men and women. In the US, heart diseases have been the leading cause of death since 2015, and the number of deaths from heart disease increased by 4.8% from 2019 to 2020. According to the Center for Disease Control and Prevention (CDC), heart disease accounts for one in every four deaths in the United States each year. These deaths are attributed to many factors ranging from undetected heart diseases causing sudden death, late detection that may damage heart muscles and require repair, or even improper monitoring after successful heart surgery. Every year more than 5 million Americans are affected by Heart Failures. Electrocardiogram (ECG), which records the electrical activity of the heart, has long been the preferred and trusted technique for doctors to detect and diagnose these heart conditions. ECG is also used for monitoring patients after the surgery for signs of trouble during recovery. Accurate ECG analysis is an important diagnostic tool in early disease detection.

SUMMARY

This present document discloses systems and methods that can be used in various embodiments to provide more robust and accurate detection of anomalies in medical images and/or electrocardiograms.

In one example aspect, a method for performing image classification includes receiving an input image having a feature of interest. The input image is associated with a mask identifying a region that includes the feature of interest. The method includes inputting the input image into a neural network engine that is trained using an objective function having a first regularization parameter and a second, different regularization parameter. The first regularization parameter indicates a first degree of sensitivity associated with samples located within the mask, and the second regularization parameter indicates a second degree of sensitivity associated with samples located outside of the mask. The method also includes identifying the feature of interest in the input image by classifying the input image using the neural network engine.

In another example aspect, a system for training a neural network engine configured to detect heart anomaly using electrocardiogram signals is disclosed. The system includes a processor that is configured to receive a set of training electrocardiogram signals. At least one electrocardiogram signal in the set of training electrocardiogram signals is associated with metadata identifying a region of interest that includes a heart anomaly. The processor is configured to input the set of training electrocardiogram signals into the neural network engine. The neural network engine is trained using an objective function having a first regularization parameter and a second regularization parameter. The first regularization parameter indicates a first degree of sensitivity associated with samples located within the region of interest, and the second regularization parameter indicates a second degree of sensitivity associated with samples located outside of the region of interest. The processor is also configured to operate the neural network engine to identify the heart anomaly by classifying the set of training electrocardiogram signals and adjust the neural network engine based on the identified heart anomaly and the metadata.

In yet another example aspect, a method for facilitating detection of one or more heart anomalies in electrocardiogram. The method includes receiving information representing a set of electrocardiogram signals and inputting the information representing the set of electrocardiogram signals into a neural network engine. The neural network engine is trained using an objective function having a regularization parameter that indicates a degree of sensitivity associated with samples located outside of a region of interest. The region of interest is determined based on gradient variation of the set of electrocardiogram signals. The method includes identifying one or more regions that include the one or more heart anomalies by classifying the set of electrocardiogram signals using the neural network engine and generating an annotated diagram corresponding to the set of electrocardiogram signals. The annotated diagram includes metadata information identifying the one or more regions that include the one or more heart anomalies.

These, and other, aspects are described in the present document.

DETAILED DESCRIPTION

Figure 1:
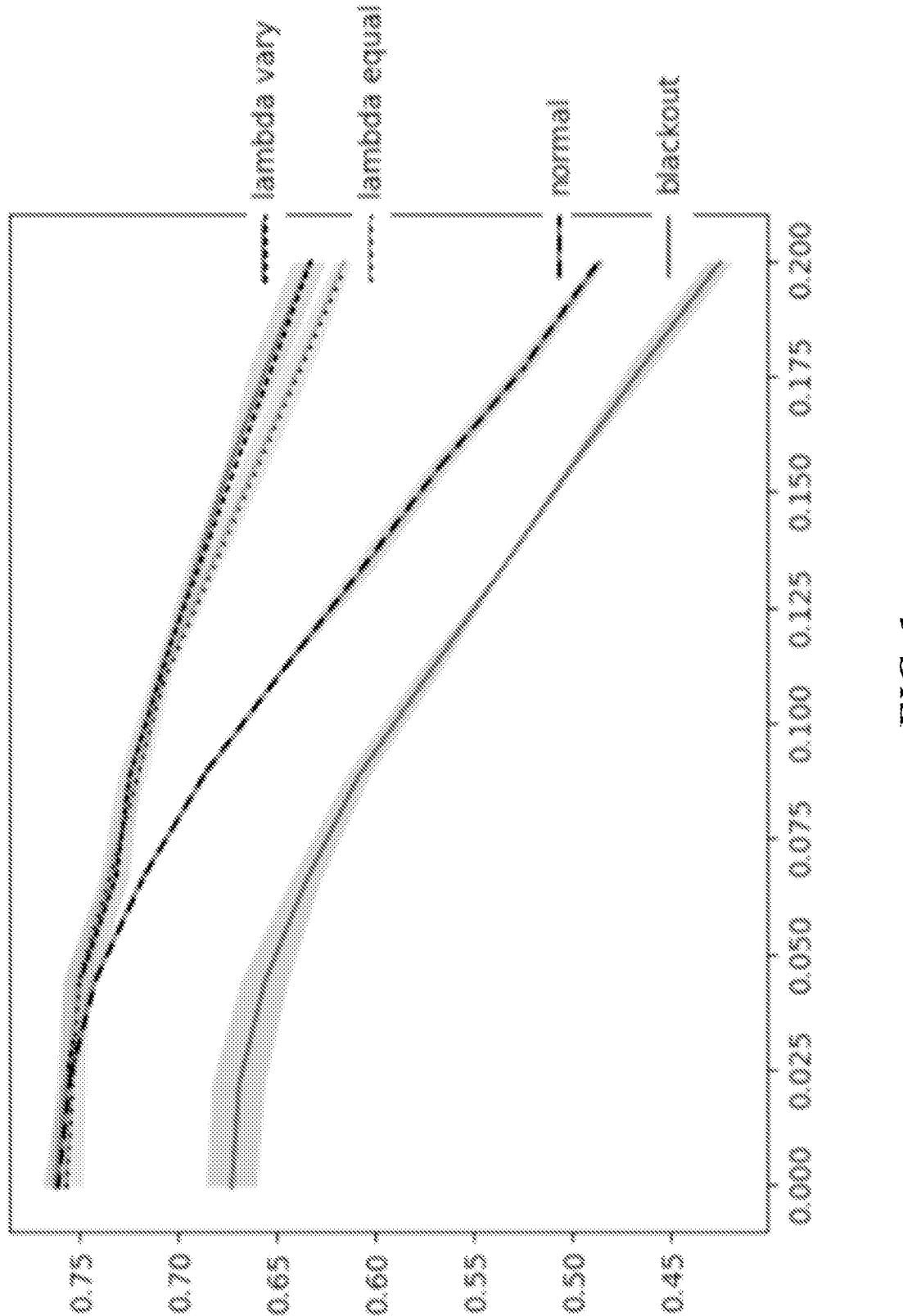
FIG. 1 is a chart illustrating example robust accuracy for the Caltech-UCSD Birds (CUB) dataset in accordance with one or more embodiments of the present technology.

Previous efforts to build conventional neural network models with improved accuracy and interpretability have been so far unsuccessful. One of the reasons for the lack of success is the lack of a comprehensive understanding of when and how learning from auxiliary information help improve the accuracy and trustworthiness of machine learning models. This patent document discloses techniques that can be implemented in various embodiments to learn from auxiliary information to improve accuracy, adversarial robustness and interpretability.

Advanced model training algorithms with the aim of improving adversarial robustness have been adopted in various fields. However, improvements on robust accuracy often come at the price of lower standard accuracy. In the context of image classification, previous methods aim at improving model accuracy and interpretability by using bounding box-based auxiliary information. For example, one of the methods penalizes the mismatch between the model-generated attention masks and bounding boxes to improve the accuracy and interpretability of convolutional neural networks (CNNs). Another method proposed using a single regularization term in the training objective that penalizes the gradients of cross entropy losses with respect to input features outside bounding boxes. The disclosed techniques incorporate a gradient-based penalty for features inside bounding boxes, thereby enabling the utilization of more refined part localization bounding box information to train the models and improves model accuracy in fine grained classification tasks.

In some embodiments, the disclosed techniques can be based on the attribution map or saliency map generation for images. Specifically, the user can specify training objectives that promotes "alignment" between such attribution maps and bounding boxes. The attribution maps are more sophisticated than conventional attribution maps in part because they are generated based on a new regularizing algorithm that have different degrees of regularization parameters. Experiments have shown that such attribution maps help improve the trustworthiness of image classifications. Finally, recent works have empirically demonstrated that adversarial robustness and interpretability are tightly connected. On one hand, adversarial robust models can generate more interpretable explanations than non-robust model. On the other, models trained to mimic gradient-based explanations of adversarially robust models exhibit more robustness. This hints at the possibility that robustness is a side-benefit of interpretability.

In some embodiments, the disclosed techniques can be implemented as an image classification neural network configured to intake auxiliary information (e.g., bounding boxes, doctor's annotations) as additional inputs. Inspired by related works on gradient-based regularization, the improved system is configured to employ a training objective (e.g., objective function) that has different degrees of regularization on different parts of inputs, which take into account auxiliary information such as, but not limited to, bounding box information and annotations. In other words, the system uses a modified objective function with at least two different degrees of regularization.

To test the accuracy and/or efficiency of the modified object function, the disclosed system was used to train and classify images in the Caltech-UCSD Birds (CUB) dataset. The image classification results (from the improved system) showed improved accuracy, robustness and interpretability, both quantitatively and qualitatively. The training and optimization methods and the results are discussed below.

Interactive Deep Learning

In some embodiments, the disclosed techniques can be implemented as a classification system that includes an interactive deep learning (IDL) neural network (e.g., engine). The IDL engine uses a new objective function having two different degrees of regularization, thereby enabling the IDL engine to continuously improve the prediction model based on human-in-the-loop feedback (e.g., interactive) resulting in significant enhancement of human abilities in many cases. In some embodiments, the IDL engine is trained to recognize various arrhythmias or anomalies in electrocardiogram (ECG) signals using one or more ECG training datasets. The IDL engine is further improved by re-training the trained neural network model using auxiliary information such as, but not limited to, users' provided bounding boxes and annotations.

In some embodiments, the IDL engine has a Long Short Term Memory (LSTM) architecture, which can be used to trained using back-propagation through time. IDL engine can also have other neural network architectures such as, but not limited to, CNN and Gated Recurrent Unit (GRU).

Once trained, the IDL engine is capable of detecting numerous heart conditions in even the longest ECG signals collected over multiple days or weeks. This automated detection saves hours of manual labor for the readers and provides them with a clear region of the ECG signals where the disease manifestation is visible, which allows them to focus on validating the results.

Figure 3A:
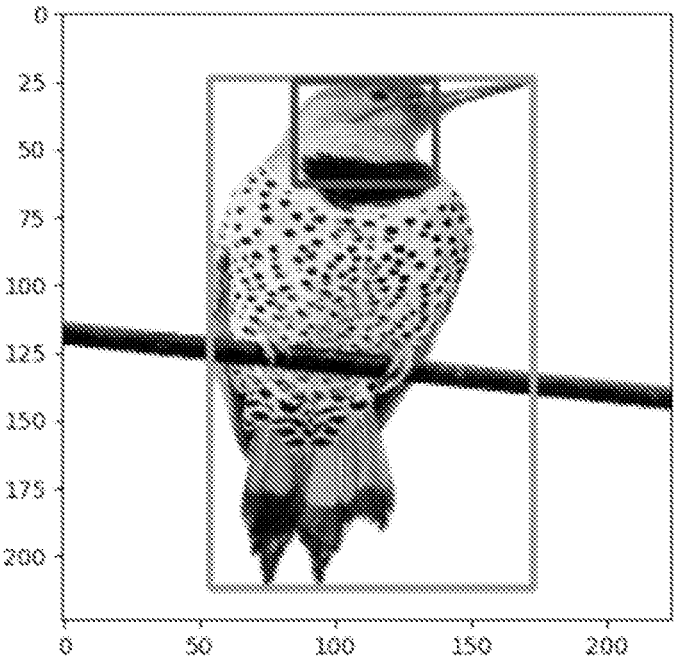
FIG. 3A illustrates an example localization accuracy concept in accordance with one or more embodiments of the present technology.
Figure 3B:
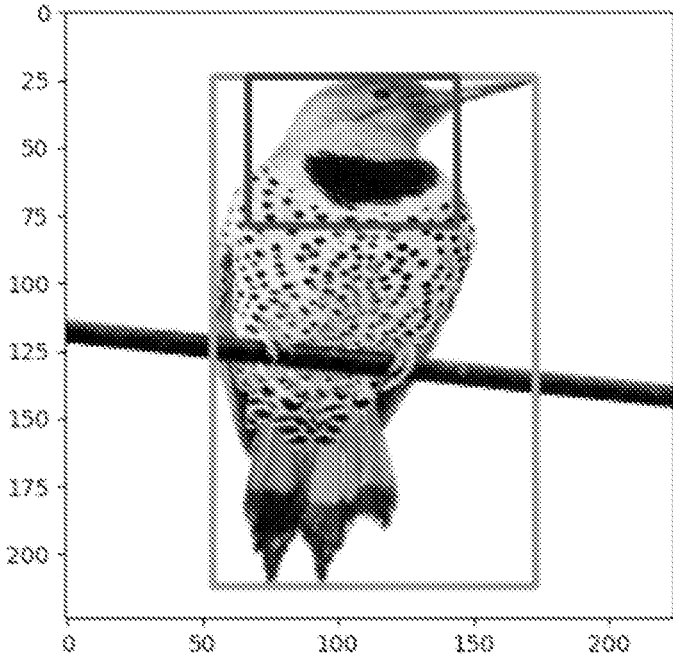
FIG. 3B illustrates another example of localization accuracy concept in accordance with one or more embodiments of the present technology.
Figure 3C:
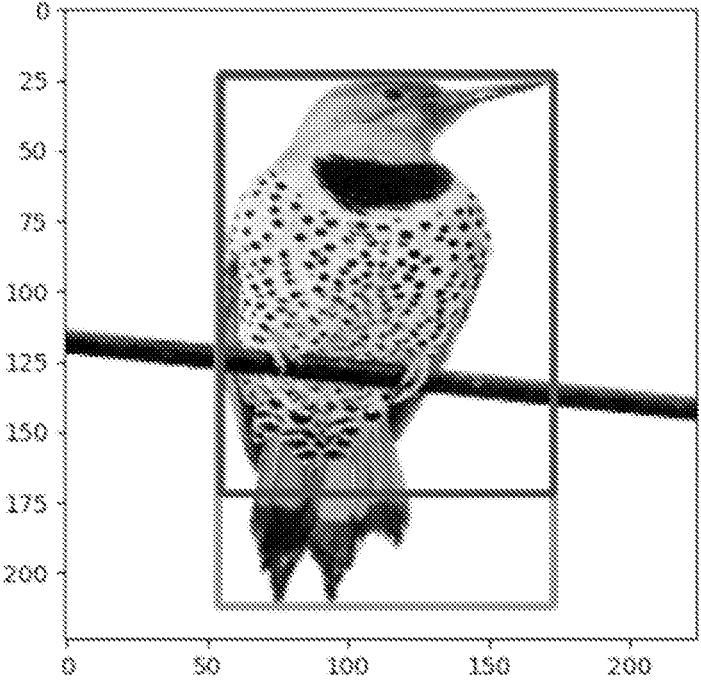
FIG. 3C illustrates another example of localization accuracy concept in accordance with one or more embodiments of the present technology.
Figure 3D:
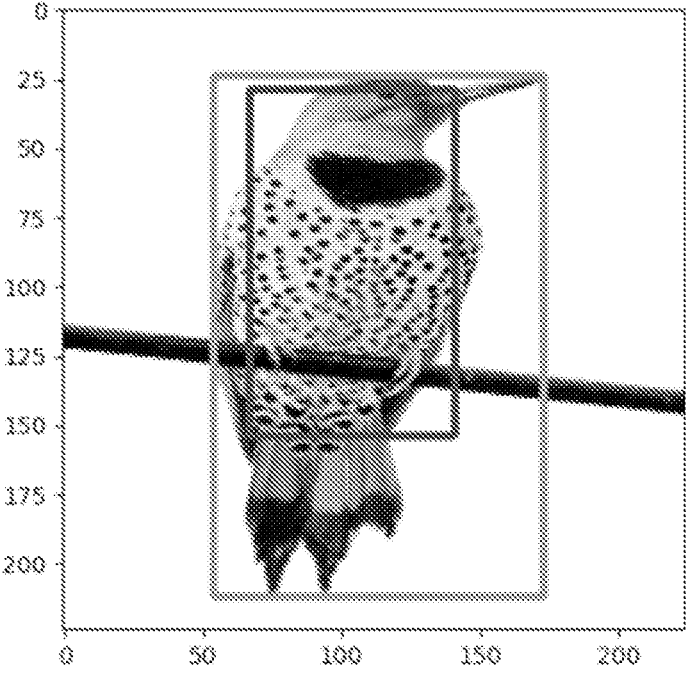
FIG. 3D illustrates yet another example of localization accuracy concept in accordance with one or more embodiments of the present technology.

To train the IDL engine to perform image classification, training data with bounding box and annotations are used. Given a set of m training examples $$\{(x_i, y_i, M_i)\}_{i=1}^m,$$

where for example i, $x_i \in \mathbb{R}d$ is its feature part (image i's pixel representation), $y_i \in [K]$ is its label part (the class of the object in the image), $M_i \subseteq [d]$ is the image's associated bounding box. An example of an image with bounding box information is given in FIG. 3A. The goal is to train a neural network-based classification model such that, when predicting on test examples, it has high accuracy, robustness and good interpretability. Formally, given an example x, our network outputs a prediction $f(x; \theta)$ that is a probability vector in $\Delta^{K-1}$, the K-dimensional probability simplex. Define the cross entropy loss of model $f(\cdot; \theta)$ on example (x; y) as $$l_{CE}(\theta, (x, y)) \triangleq \ln \frac{1}{f^y(x; \theta)},$$

where $z^j$ denotes the j-th coordinate of vector z.

For model training, the following objective function is optimized:

$$\min_\theta \sum_{i=1}^m l(\theta, (x_i, y_i, M_i)), \qquad \text{Eq. (1)}$$

where $l(\theta, (x, y, M)) \triangleq$ $$l_{CE}(\theta, (x, y)) + \lambda_1 \sum_{j \in M} \left( \frac{\partial l_{CE}(\theta, (x, y))}{\partial x^j} \right)^2 + \lambda_2 \sum_{j \in [d] \setminus M} \left( \frac{\partial l_{CE}(\theta, (x, y))}{\partial x^j} \right)^2$$

for some $\lambda_1, \lambda_2 > 0$. In addition to minimizing the usual cross entropy loss, it is important to ensure that the model's predictions have different degrees of sensitivity to different parts of the training images. Specifically, the magnitude of $$\frac{\partial l_{CE}(\theta, (x, y))}{\partial x^j}$$

characterizes the sensitivity of the cross-entropy loss with respect to the j-th pixel. The IDL engine or model is trained such that the sensitivity to input aligns with object bounding boxes as much as possible; formally, $$\frac{\partial l_{CE}(\theta, (x, y))}{\partial x^j}$$

should be large for j in M and should be small otherwise.

In some embodiments, the objective function used to train the above IDL model set $\lambda_1$ and $\lambda_2$ at values greater than zero and different from each other. In contrast, the objective function of some conventional methods sets $\lambda_1 = \lambda_2$, which degenerates the objective function to that of double back-propagation function.

To illustrate the improved accuracy, robustness and interpretability of the IDL engine of the disclosed system, the CUB dataset was used to train and test the IDL engine. CUB has approximately 11,788 examples. The data preparation process takes the union of the train and test sets provided by the CUB dataset, permute the set, and perform a three-way split. The first split consists of ½ of the data, which is used for training. The remaining data is divided into three sets of equal sizes: the first set is used to select the best model during training, the second for $\lambda_1$ and $\lambda_2$ hyperparameter selection and the third set is used for testing. In some embodiments, the ResNet architecture was selected. Training was performed with mini-batch stochastic gradient descent and a learning rate of 0.001. It should be noted that other learning rate is possible such as, but not limited to, 0.005 and 0.01. Training with the choices of $\lambda_1$ and $\lambda_2$ in $\Lambda^2$ was considered, where $$\Lambda = \{0\} \cup \left\{ \left( \sqrt[3]{10} \right)^i : i \in \{-3, -2, \ldots, 9\} \right\}.$$

The following set of algorithms was evaluated:

$\lambda$-VARY: train a model for each $(\lambda_1, \lambda_2)$ in $\Lambda^2$, and use the validation set to select the best performing model.

$\lambda$-EQUAL: train a model for each $(\lambda_1, \lambda_2)$ in $\{(\lambda_1, \lambda_2) \in \Lambda^2 : \lambda_1 = \lambda_2\}$, and use the validation set to select the best performing model.

BLACKOUT: train a model that minimizes the cross-entropy loss over modified training data $(\tilde{x}_i, y_i)$; here for each i, $\tilde{x}_i$ is defined as $x_i$ with all coordinates j in $M_i$ set to zero.

STANDARD: standard training that minimizes the cross-entropy loss over $(x_i; y_i)$'s; this is also equivalent to setting $\lambda_1 = \lambda_2 = 0$.

All experiments are repeated three times to generate heatmaps identifying the best performing models and their corresponding $\lambda_1$ and $\lambda_2$ values. In other words, many versions of the IDL engines were created by training each version with a different set of $\lambda_1$ and $\lambda_2$ values. In some embodiments, the desired regularization parameters for the trained model can be determined by balancing robust accuracy (e.g., FIG. 4), saliency value (e.g., FIG. 5), and/or localization accuracy (e.g., FIG. 6) to achieve the optimal classification results. The best performing IDL engine is the engine with the highest performance measure of the test dataset.

Standard and Robust Accuracy Comparison

The adversarial robustness of the trained IDL models are tested for 10 values of adversarial perturbation radii $\in$'s in $$\left\{ \frac{0.2i}{9} : \in \{0, \ldots, 9\} \right\}$$

using the Fast Gradient Sign Method. All adversarial tests were performed using the Foolbox library, which is an adversarial attack tool library. It should be noted that other adversarial attack libraries can also be used.

Figure 4:
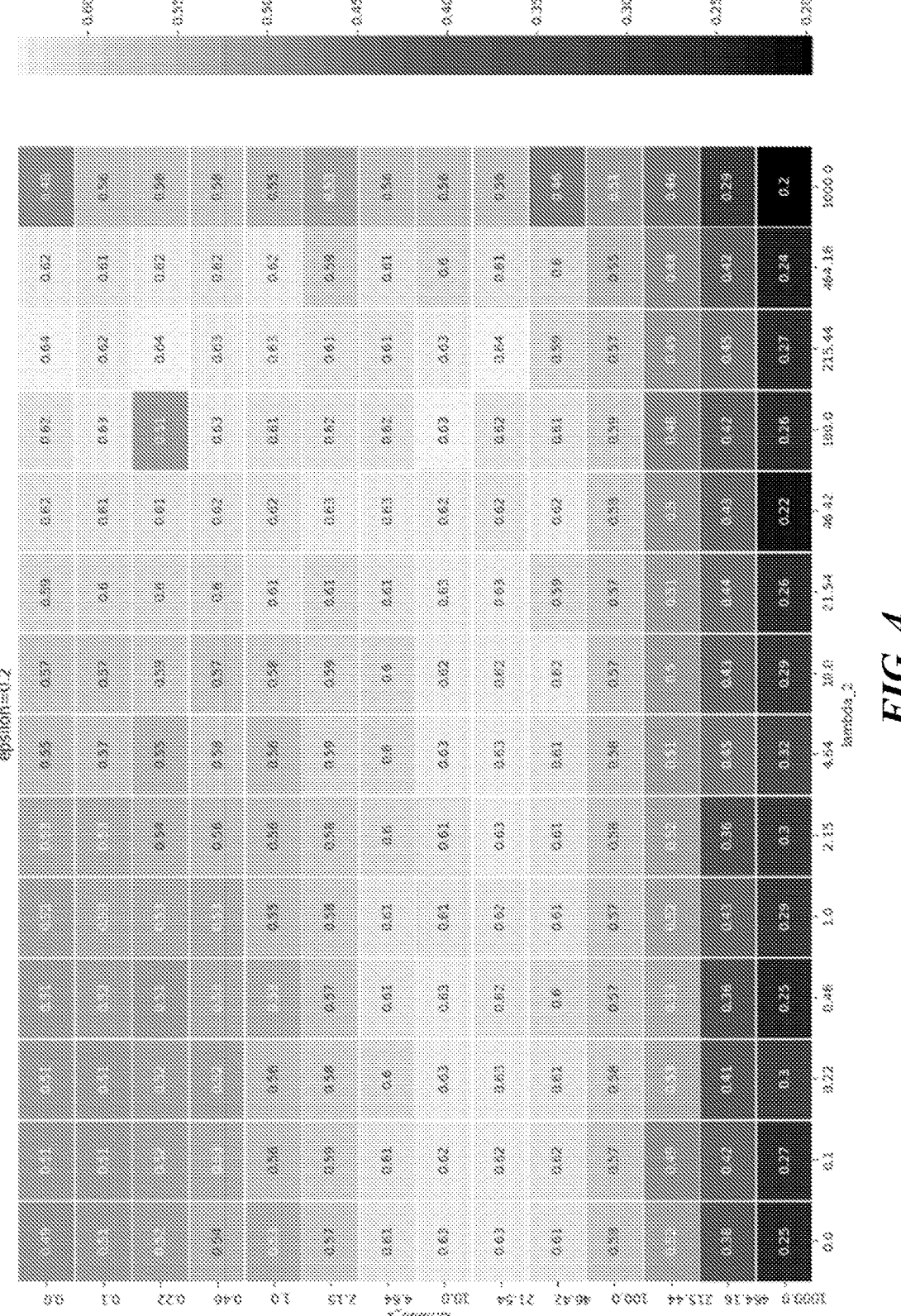
FIG. 4 is a chart illustrating example robust accuracy of trained interactive deep learning (IDL) models in accordance with one or more embodiments of the present technology.

Referring to FIG. 4, which shows the robust accuracy heatmap generated by training and validating 196 different trained IDL models. Each IDL model is trained using a different set of $\lambda_1$ and $\lambda_2$. Each cell indicates the performance of each trained IDL model on the validation dataset. Using the heatmap, the best IDL model can be identified.

Recall that for $\lambda$-VARY and $\lambda$-EQUAL, for each value of $\in$, separate values of $(\lambda_1, \lambda_2)$ pairs are chosen using the validation set. The results are shown in FIG. 1, which illustrate test robust accuracy for different value of $\in$'s for the CUB dataset. It can be seen that $\lambda$-VARY trains models that have higher standard accuracy and also robust to adversarial attacks; the performance of the learned models beat those of $\lambda$-EQUAL (especially when E is large), showing the utility of incorporating bounding box information in the training objective.

Interpretability Comparison

Figure 2A:
FIG. 2A illustrates a picture of a bird that will undergo the process of saliency mapping.
Figure 2B:
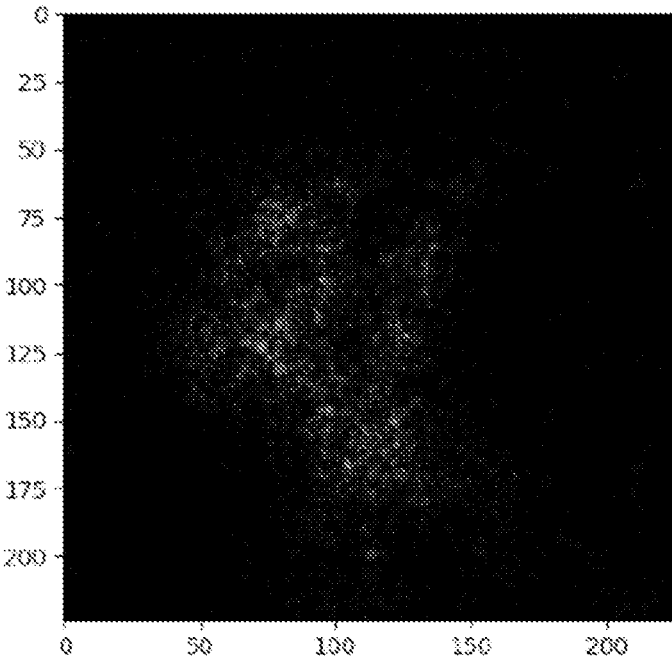
FIG. 2B illustrate a saliency map generated in accordance with one or more embodiments of the present technology.
Figure 2C:
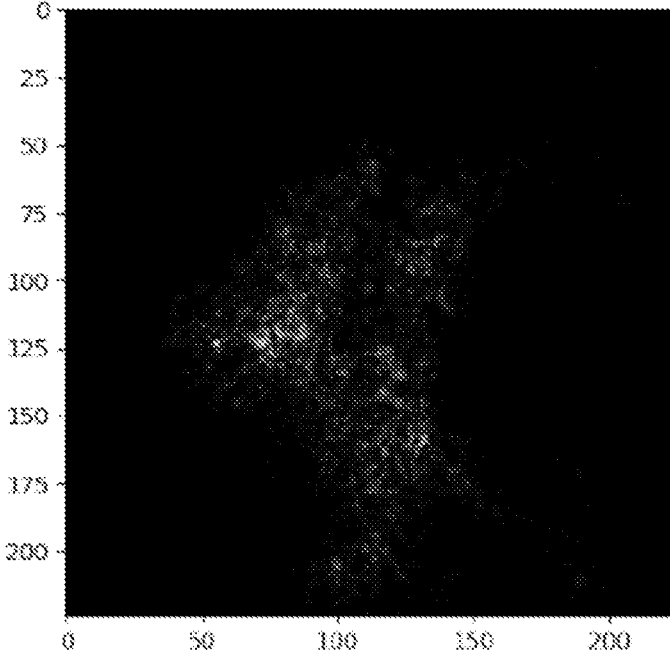
FIG. 2C illustrate another saliency map generated in accordance with one or more embodiments of the present technology.
Figure 2D:
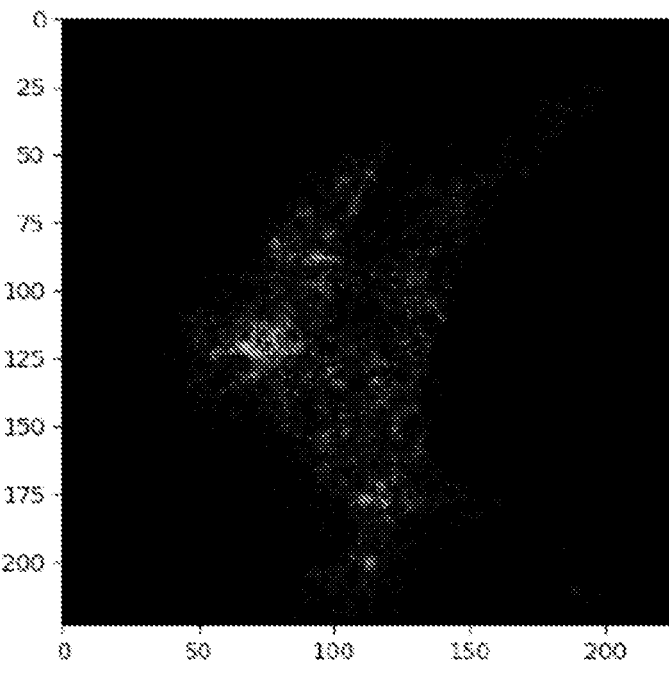
FIG. 2D illustrate another saliency map generated in accordance with one or more embodiments of the present technology.
Figure 2E:
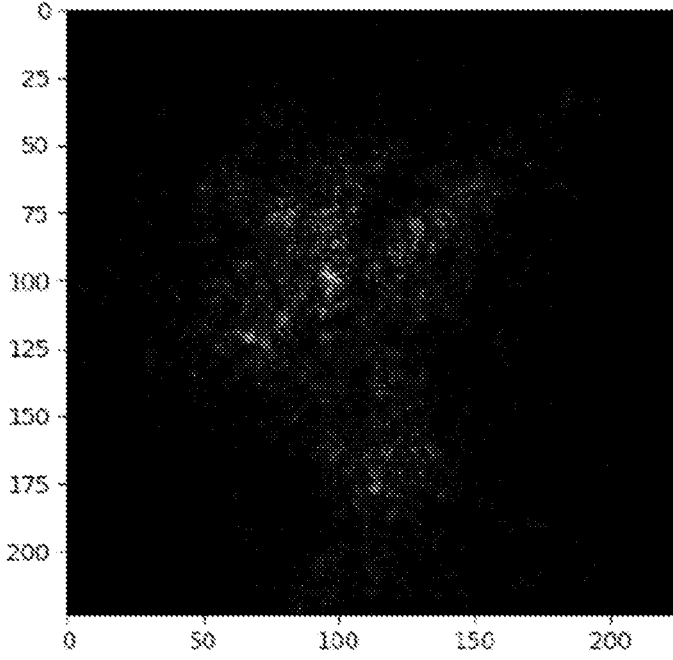
FIG. 2E illustrate yet another saliency map generated in accordance with one or more embodiments of the present technology.

The interpretability comparison process compares the interpretability of the trained models both qualitatively and quantitatively. The gradient-based saliency map, generated by the model trained by each algorithm on a few bird images in the CUB dataset, is plotted. FIG. 2B shows the saliency map of the STANDARD parameter where saliency features are dispersed and clearly not focusing on the bird body. FIG. 2C shows the saliency map of $\lambda$-EQUAL. As shown, the saliency features are better than STANDARD as they exhibit more a bird shape. FIG. 2D shows the model trained by $\lambda$-VARY, which shows the complete shape of bird and even with highlights on the subtle parts such as beaks and legs. The saliency map of the BLACKOUT model (FIG. 2E) is reasonably moderate. But obviously, it does not perform as well as the $\lambda$-VARY model.

Quantitative Results

To quantitatively measure the interpretability of the gradient-based saliency maps output by different IDL models (generated using different sets of $\lambda_1$ and $\lambda_2$), bounding boxes were extracted from the test images of the test dataset. The bounding boxes were evaluated by: employing the saliency metric shown in Table 1; and comparing the extracted bounding boxes with the original bounding boxes using localization accuracy. To generate a bounding box from a saliency map, the image is binarized by thresholding, and the tightest rectangular box that contains the pixels whose grayscale is above the threshold is outputted.

TABLE 1

Saliency metric comparison among the evaluated methods.

| STANDARD | BLACKOUT | $\lambda$-EQUAL | $\lambda$-VARY |
|---|---|---|---|
| $0.466 \pm 0.047$ | $0.396 \pm 0.033$ | $0.343 \pm 0.02$ | $0.283 \pm 0.03$ |

To measure the quality of our saliency map, after generating a bounding box, the corresponding region from the original image is cropped and is passed into the network to make prediction. The saliency metric is defined as: $s(a,p)=\log(a)-\log(p)$, where $a=\max(0.05; \hat{a})$, and $\hat{a}$ is the area fraction of the bounding box, and p is the model's predictive probability for the correct label. The lower value the saliency metric the better. Table 1 shows the lowest saliency value for each evaluated method (i.e., standard, blackout, $\lambda$-EQUAL, and $\lambda$-VARY) trained by all methods on the CUB dataset. As shown in Table 1, $\lambda$-VARY outperforms all baselines by having the lowest saliency value.

Figure 5:
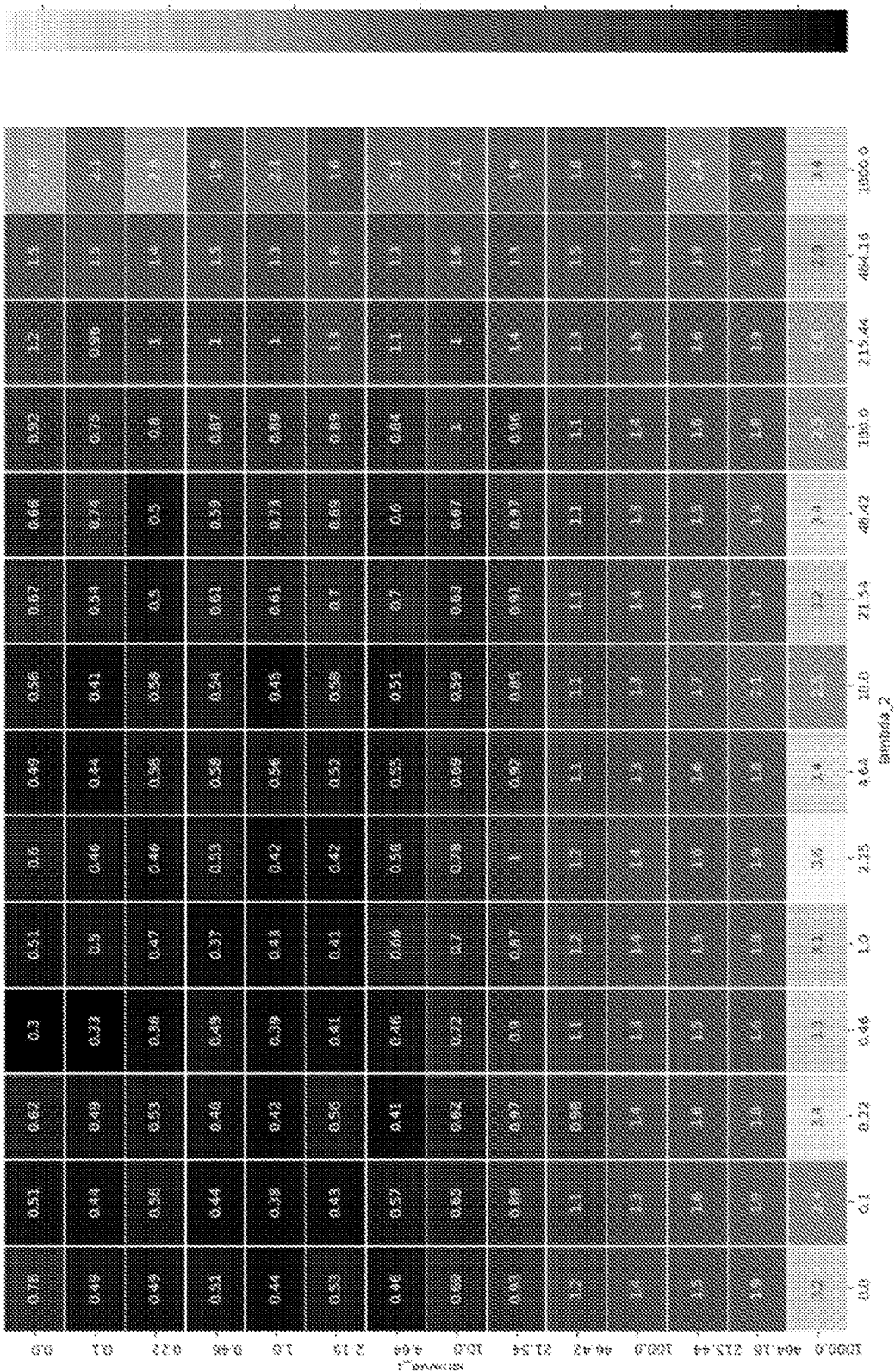
FIG. 5 is a chart illustrating example saliency measure of trained IDL models in accordance with one or more embodiments of the present technology.

Referring to FIG. 5, which shows the saliency heat map generated by training and validating 196 different trained IDL models. Each IDL model is trained using a different set of $\lambda_1$ and $\lambda_2$. Each cell indicates the performance of each trained IDL model on the validation dataset. For the saliency heatmap, the lower the cell value the better the performance.

Localization Accuracy

The localization accuracy is defined as the fraction of examples where the model prediction is correct and the generated bounding box (FIGS. 3A-3D) has intersection over union (IOU) value of $\geq 0.5$ with the ground truth bounding box. Table 2 shows the test localization accuracy of models trained by all methods on the CUB dataset, where $\lambda$-VARY outperforms all baselines (the larger the better).

Figure 6:
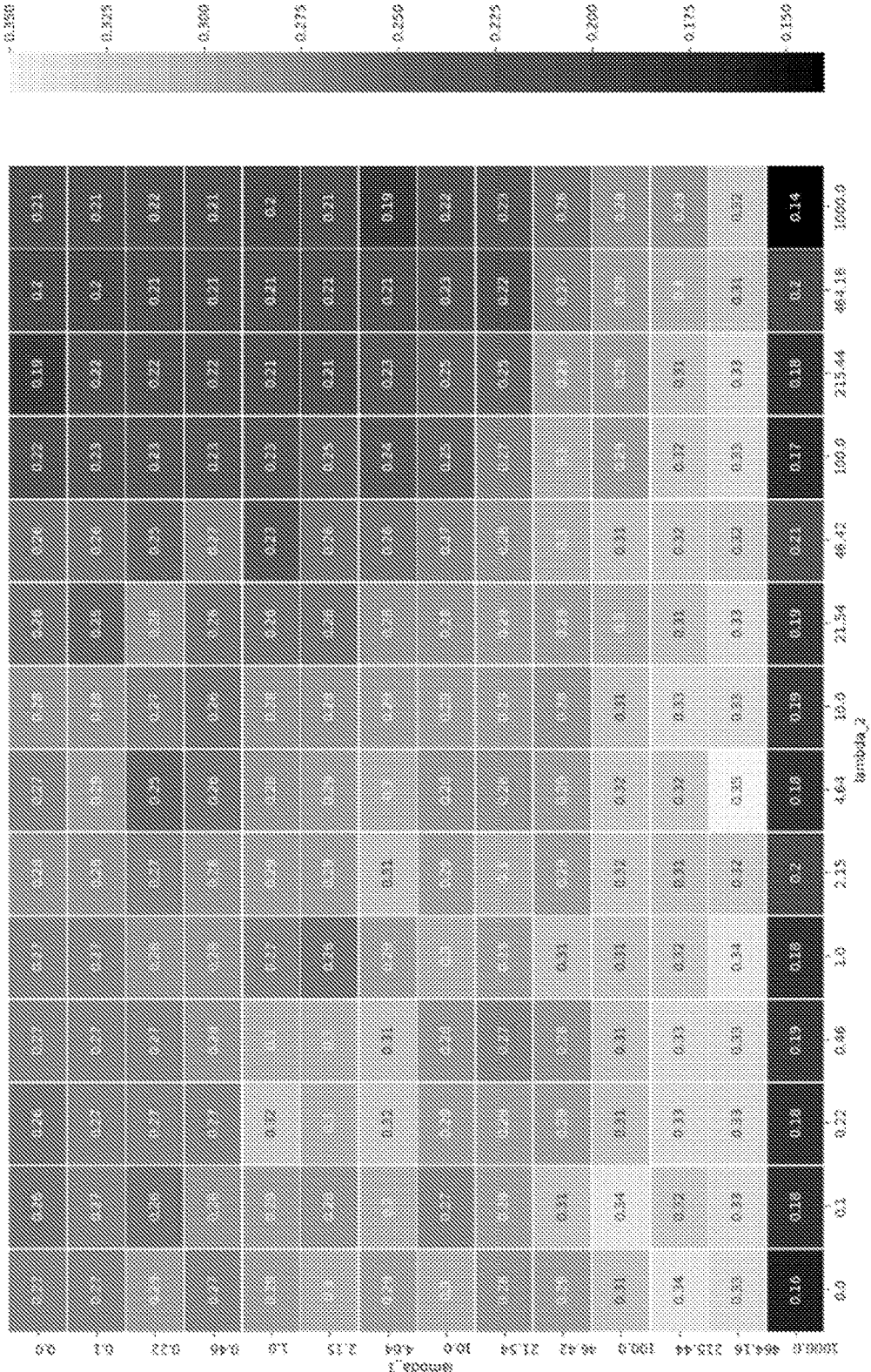
FIG. 6 is a chart illustrating example localization accuracy of trained IDL models in accordance with one or more embodiments of the present technology.

FIG. 6 illustrates the localization accuracy heatmap generated by training and validating 196 different trained IDL models. Each IDL model is trained using a different set of $\lambda_1$ and $\lambda_2$. Each cell indicates the performance of each trained IDL model on the validation dataset. Using the heatmap, the best IDL model can be identified. Here, the higher the cell value the better the performance.

TABLE 2

Localization accuracy comparison among the evaluated methods.

| STANDARD | BLACKOUT | $\lambda$-EQUAL | $\lambda$-VARY |
|---|---|---|---|
| $0.236 \pm 0.02$ | $0.30 \pm 0.021$ | $0.30 \pm 0.169$ | $0.343 + 0.012$ |

IDL Engine for ECG Classification

Accurate ECG interpretation is critical in detecting heart diseases. However, they are often misinterpreted due to a lack of training or insufficient time spent to detect minute anomalies. A recent study found that 30% of myocardial infarction events were misclassified as low risk, with ECG misinterpretation responsible for half of the misclassifications. Misdiagnosis is also a top concern expressed by cardiac patients.

The automation of ECG reading has been a long-standing need. Analyzing the ECG signals manually requires extreme concentration, causes mental fatigue, and is not reimbursed adequately by the insurance companies. Consequently, the number of people who can read ECG signals is shrinking, and experienced doctors do not have enough time to scrutinize patients' ECGs. However, commercial ECG machines only provide preliminary processing and analysis, and offer limited assistance in detection of more complex cardiac conditions.

The machine learning community observed this need, and numerous machine learning algorithms have been proposed for disease detection. For example, Convolutional Neural Network (CNN) has been used to assist arrhythmia and myocardial detection. Other algorithms such as decision trees, k-nearest neighbor, logistic regression, support vector machines, and inception neural networks have also been evaluated. While existing machine learning algorithms have succeeded in classifying basic cardiac conditions, classification of more complex cardiac events remains challenging. Furthermore, existing solutions provide diagnosis in a black-box manner, requiring the medical personnel to carefully analyze the ECG again to validate the algorithm's interpretations.

The disclosed techniques can adaptively adjust the detection algorithms based on feedback collected from expert ECG readers. In some embodiments, the disclosed techniques can be implemented as a signal importance mask feedback-based machine learning system that accepts expert feedback continuously (e.g., for online learning) or in a periodic/aperiodic manner (e.g., for offline learning). In some embodiments, the system can provide medical personnel with a precise region of the ECG signals where the disease manifestation is visible. In some embodiments, a visual representation of the system's decision process can be shown to the medical personnel to illustrate what portion of the signal is used in the decision process, thereby enabling the medical personnel to quickly validate the results or correct areas of misinterpretation without the need to fully reexamine the ECG again.

Figure 7:
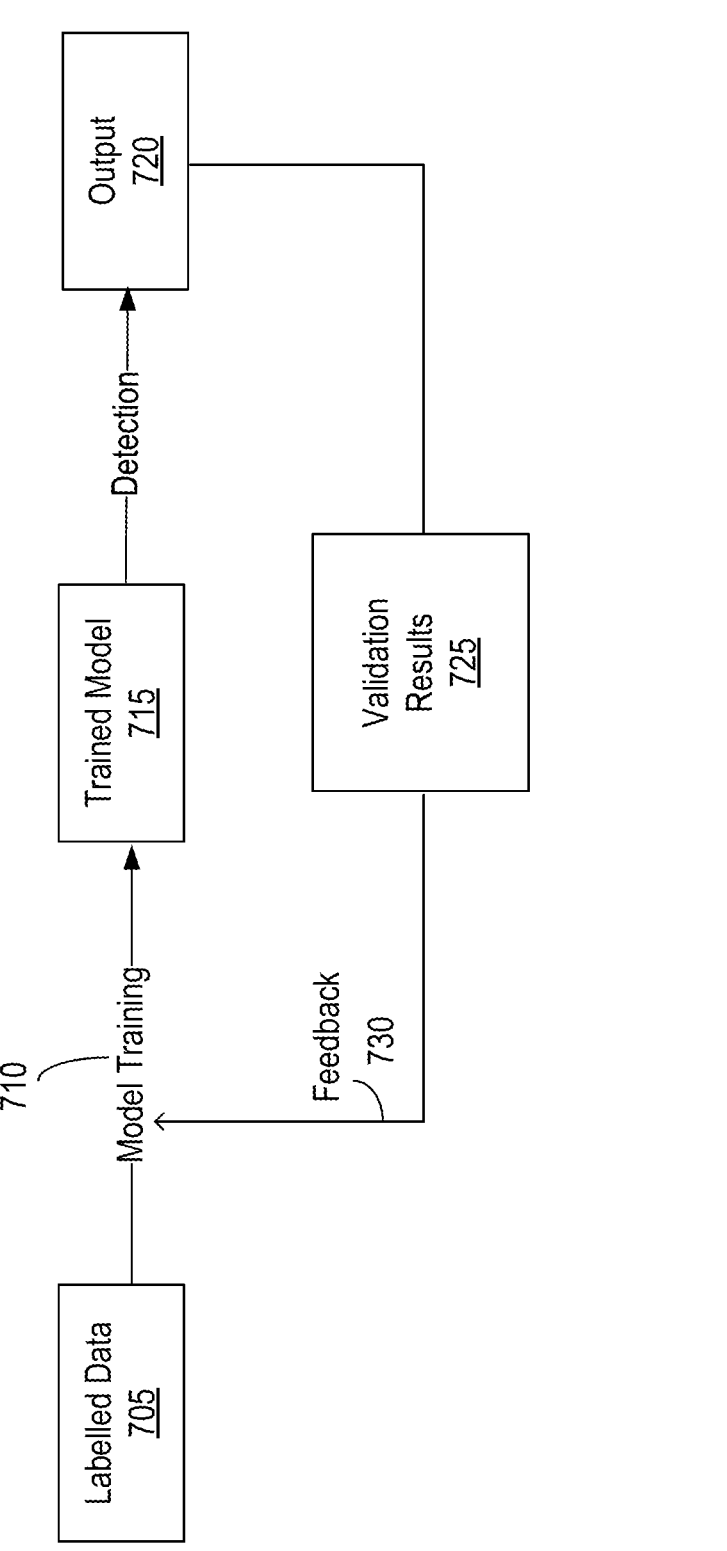
FIG. 7 is a flowchart illustrating a training, validation, and re-training process in accordance with one or more embodiments of the present technology.
Figure 8:
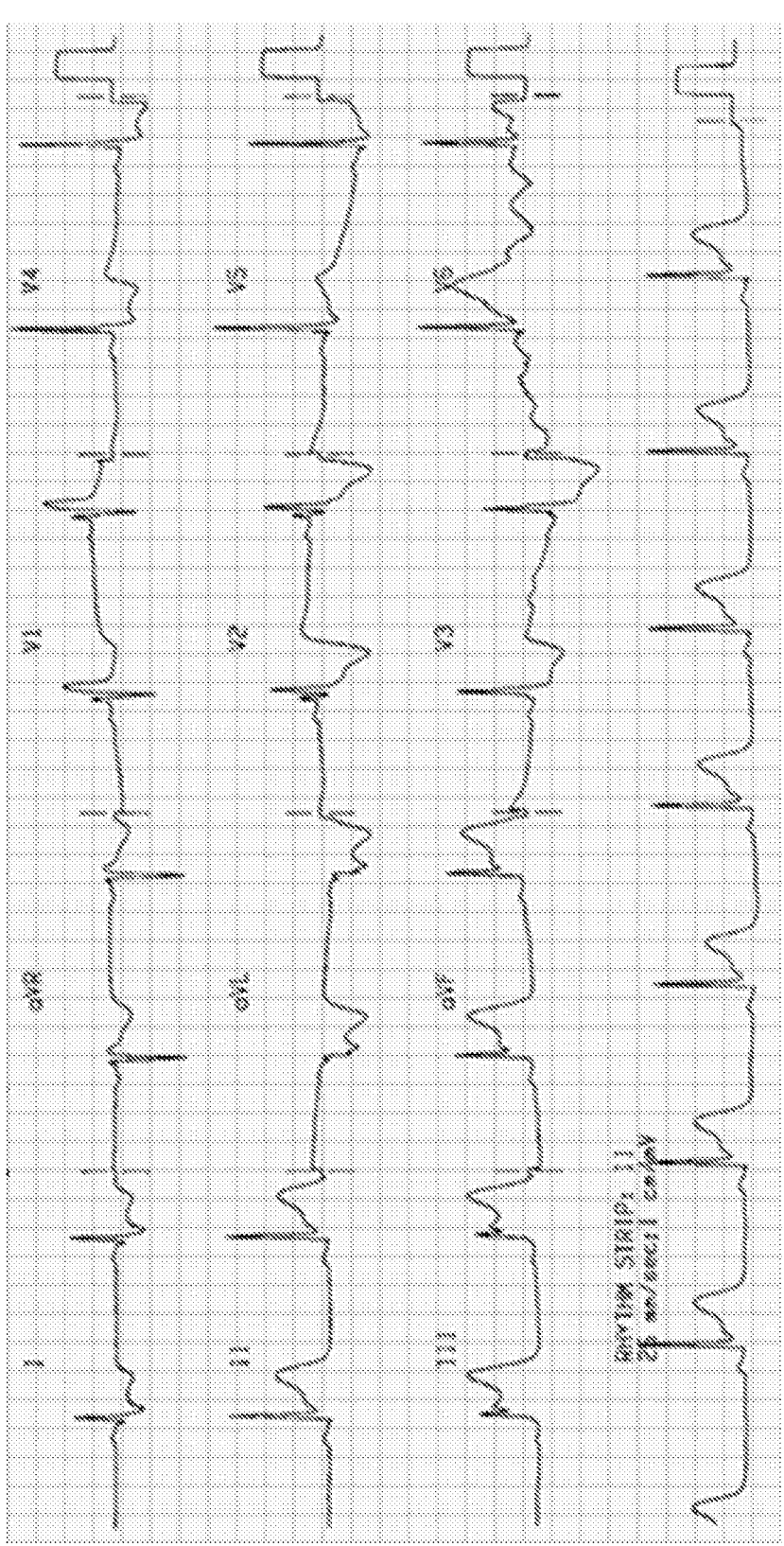
FIG. 8 illustrates example ECG data.

FIG. 7 illustrates a training process 700 for training an IDL model (e.g., neural network, engine) in accordance with some embodiments of the present disclosure. Process 700 starts at Operation 705 where a training dataset is prepared and used to train the IDL model. For ECG classification, the training dataset can include thousands of labelled ECG data that can include ECG data of healthy heart signals and abnormal heart signals. An example of labelled ECG data is shown in FIG. 8. It should be noted that the label can be in the form of metadata.

In some embodiments, process 700 can use the open source ECG data from Physionet for training, which may include unlabeled ECG data. The training process 700 can query a database to receive expert feedback associated with one or more ECG signals. For example, the feedback can be returned in the form of metadata associated with the corresponding training data. The training process 700 can associate the unlabeled ECG data with the metadata to prepare labelled ECG data such as shown in FIG. 8.

Once the training data set is prepared, the model is trained at Operation 710 using an objective function to create a trained model 715. The trained model is then used to classify a validation dataset and/or real patient ECG data at Operation 720.

ECG data can be represented using one-dimensional data. Specifically, the training data can be represented as a set of tuples $$\{(x_i, y_i)\}_{i=1}^{n},$$

where for each example i, $x_i \in R^d$ is ECG signal representation. In selected example ECG datasets for training 71-way heart disease classification from 12-lead ECG signals, d=12×300 and $y_i \in \{-1, 1\}^K$ is the class labeling, where K=71 for each coordinate $j \in =(1, \ldots, K)$. $y_j=-1$ and +1 indicate that label j is present and absent, respectively. The training data can also include signal importance masks $M_i \subset \{1, \ldots, d\}$ for at least part of the samples. The index set of samples having corresponding signal importance masks is denote by E.

As compared to detecting features of interest in image data, it is easier to distinguish sample values and detect the ECG signal given a set of input data. Therefore, only the sensitivity of the loss with respect to the irrelevant features need to be penalized. In some embodiments, one of the two regularization parameters can be set to 0 for ECG data training. For example, the model can be represented by a function f(x; θ), where x represents the ECG signal and θ represents the model parameter. Given x, θ, the model output f(x; θ) lies in $R^K$. The multi-label classification result can be denoted using sign(f(x; θ)):=(sign(f(x; θ)$_1$), . . . , sign(f(x; θ)$_K$))∈{−1, 1}$^K$, wherein sign(z)=1 if z>0 and sign(z)=−1 otherwise. The training process hinge on finding θ that has a small average multi-label logistic loss on the training examples. Here, the multi-label logistic loss of model f(•; θ) on example (x,y) is defined as $$l_{logistic}(\theta, (x, y)) = \sum_{j=1}^{K} \ln(1 + \exp(-y_j f_j(x; \theta))).$$

The training objective function can be a regularized loss objective that takes advantage of signal importance masks, defined as:

$$\min_{\theta}\left(\sum_{i \in E} l_\lambda(\theta, (x_i, y_i, M_i)) + \sum_{i \notin E} l_{logistic}(\theta, (x_i, y_i))\right), \quad \text{Eq. (2)}$$

where $l_\lambda(\theta, (x, y, M)) :=$ $$l_{logistic}(\theta, (x, y)) + \lambda_2 \sum_{j \in [d] \setminus M}\left(\frac{\partial l_{logistic}(\theta, (x, y))}{\partial x^j}\right)^2$$

Here, $\lambda_1=0$ and $\lambda_2>0$. Sample (x,y) can be viewed as introducing two parts of losses that contribute to the training objective: the first part is the standard multi-label logistic loss $l_{logistic}(\theta,(x,y))$ and the second part is $$\sum_{j \in [d] \setminus M}\left(\frac{\partial l_{logistic}(\theta, (x, y))}{\partial x^j}\right)^2$$

which applies to samples in E whose signal importance mask M is available. This term regularizes the sensitivity of the model with respect to the input using the signal importance masks: it penalizes the model from being too sensitive to parts of the ECGs outside their corresponding signal importance masks.

In some embodiments, two different regularization parameters can be used for ECG data training to achieve greater robustness. An objective function such as shown in Eq. (1) can be used to regularize the sensitivity of the model with respect to the input using the signal importance masks.

Referring back to Operation 720, the trained IDL model makes prediction(s) on the patient's heart condition, while also pinpoints parts of the ECG that are responsible for its prediction. For example, system 700 can be configured to highlight the difference in peaks in the ECG (e.g., gradient changes in the ECG signal indicating the important regions). Alternatively, or in addition, the system 700 can provide additional information (e.g., graphical or textual) associated with how the important regions are determined. In this way, the results can be readily interpreted, trusted, and acceptable to the medical practitioner, without the need for the medical practitioner to completely re-examine the ECG data again.

Figure 9:
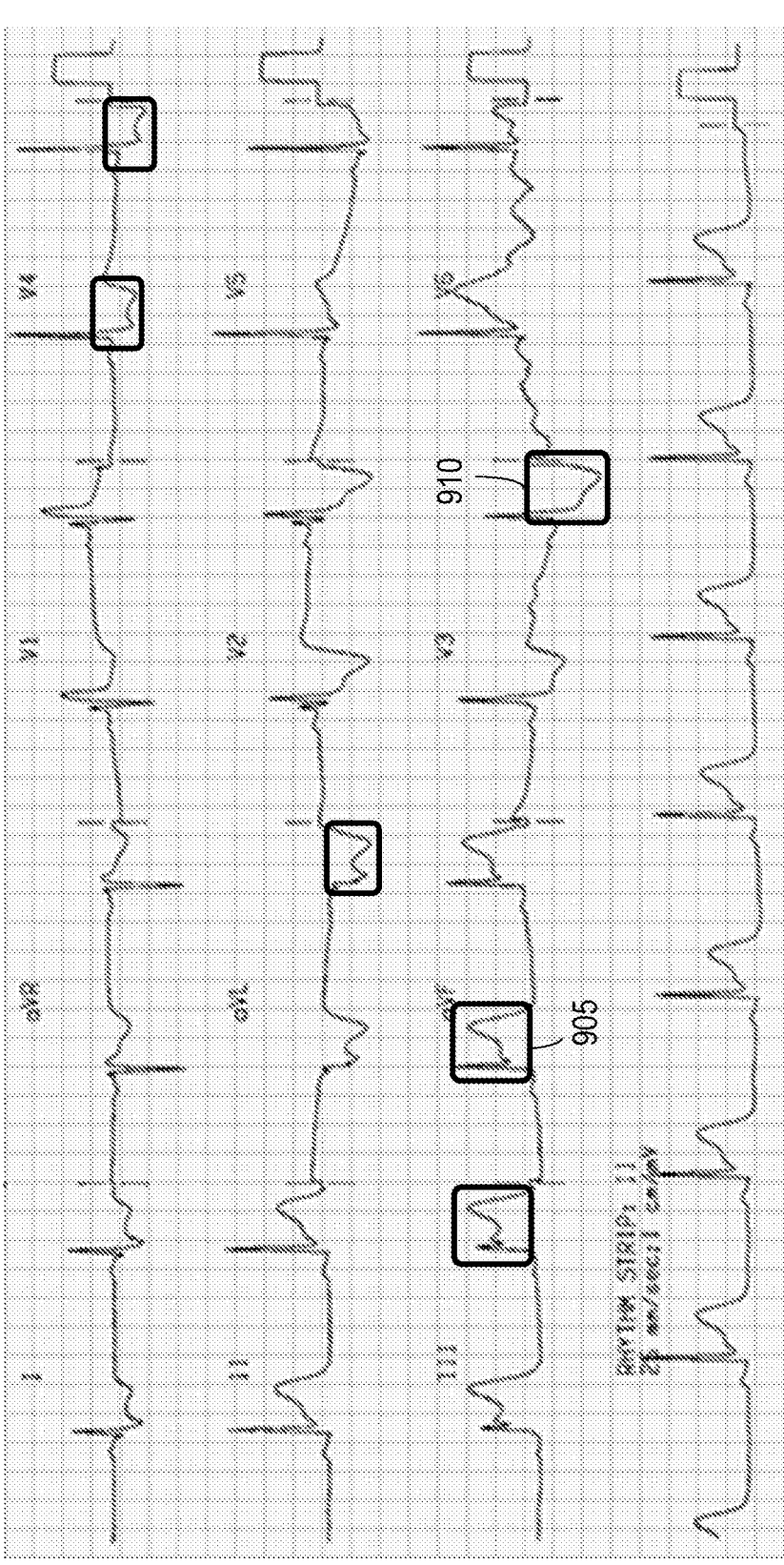
FIG. 9 illustrates example auxiliary information for the ECG data shown in FIG. 8 in accordance with one or more embodiments of the present technology.

The results are then validated and annotated by the medical practitioner at Operation 725. The doctors can also help the trained model to better focus on the important region(s) of the ECG by drawing in bounding boxes 905, 910, and 915. Each bounding box can be annotated (text not shown) to explain the anomaly or arrhythmia. FIG. 9 illustrates an example of an annotated ECG data with bounding boxes. Here, the medical practitioner can either confirm the system's finding and/or highlight (e.g., draw bounding box) and annotate missing diagnosis.

At Operation 730, images with manually inputted bounding boxes and corresponding auxiliary data (e.g., annotation) are fed back into the training algorithm to improve the IDL model. In some embodiments, the auxiliary data is provided during the training process (e.g., during online training) to adaptively improve the IDL model while the IDL model is being trained. In some embodiments, the IDL model is retrained after feedback information is collected and stored in a data base. The feedback information is retrieved prior to the IDL model is retrained.

Figure 10A:
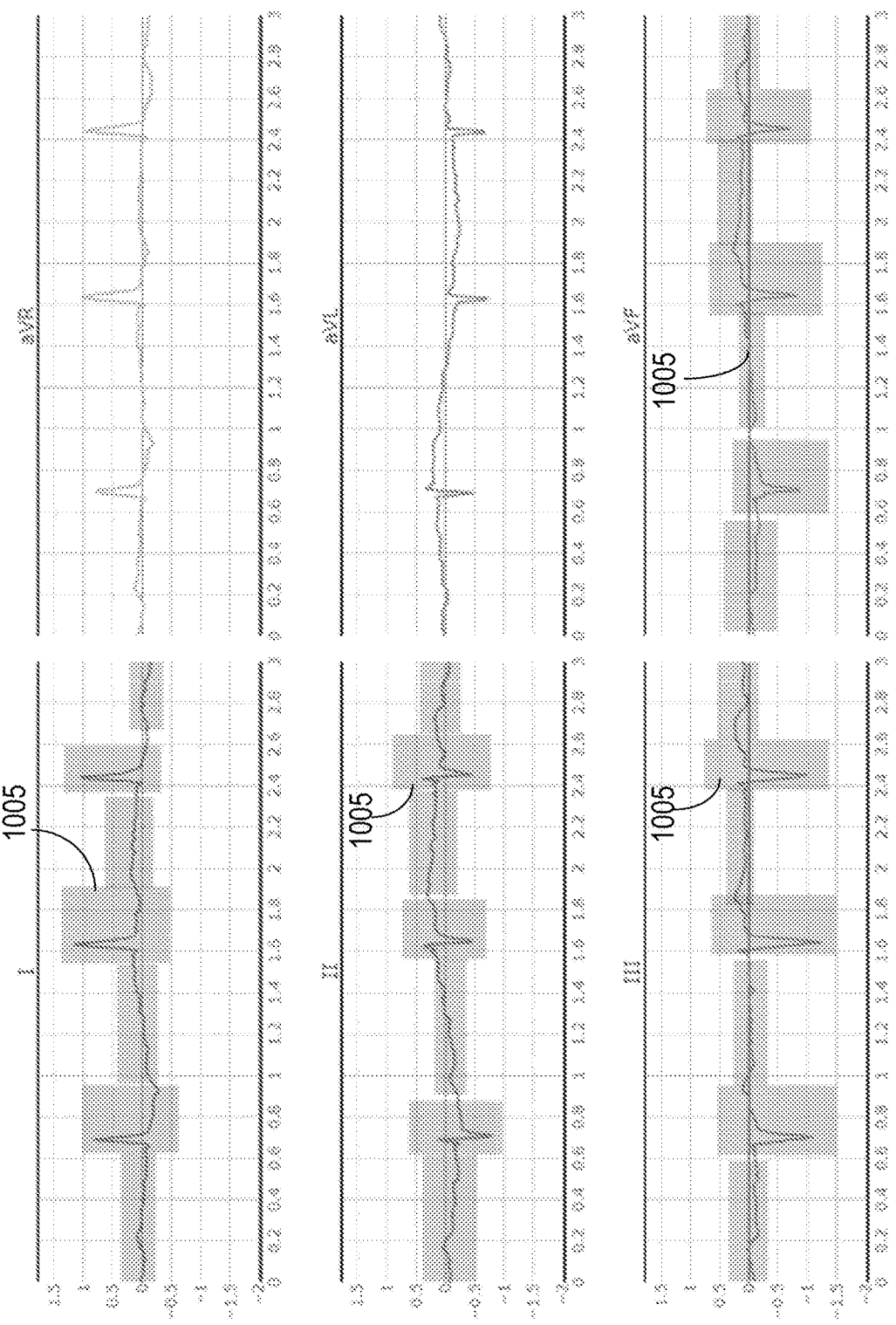
FIG. 10A illustrates example feedback collected for ECG model training in accordance with one or more embodiments of the present technology.
Figure 10B:
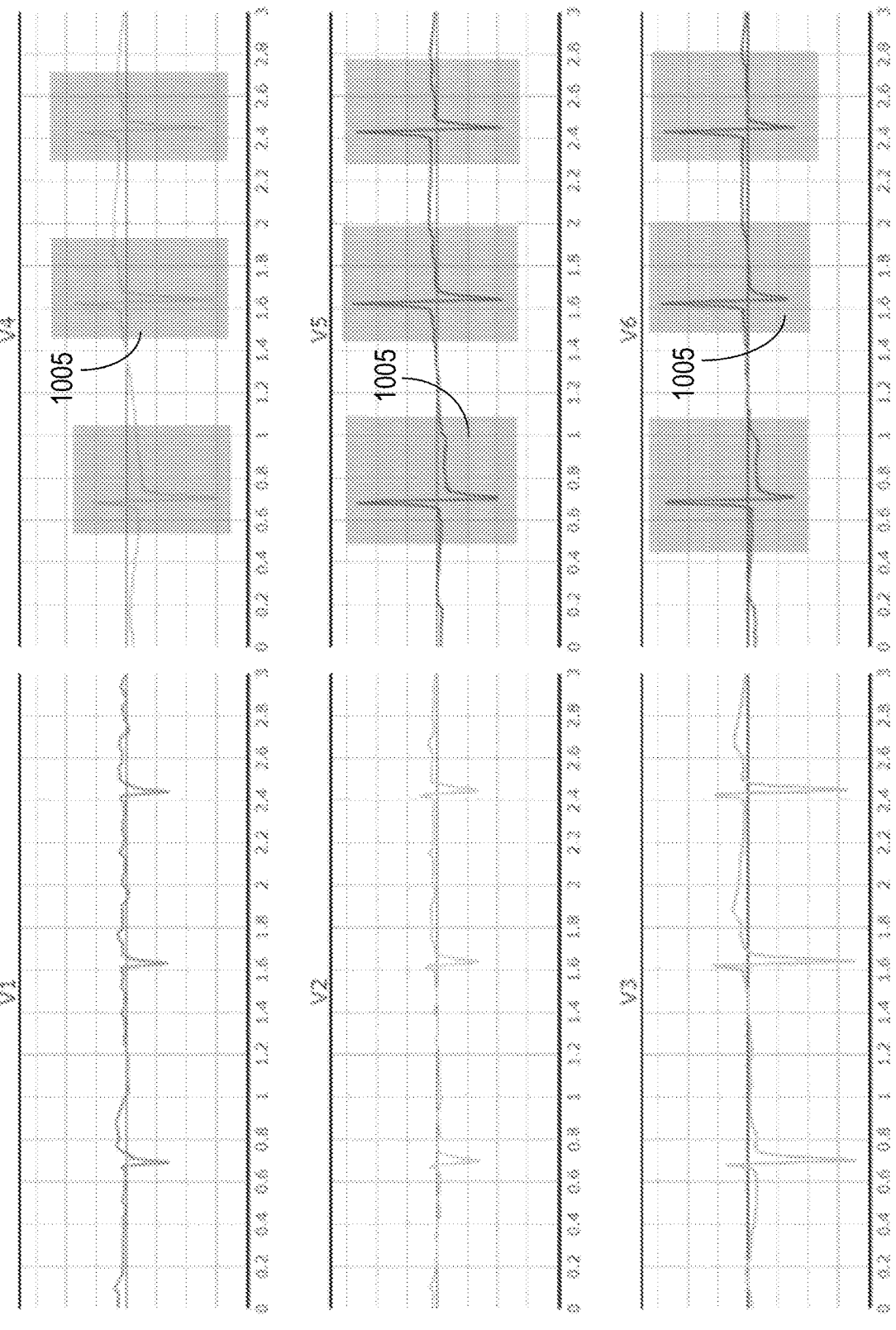
FIG. 10B illustrates additional example feedback collected for ECG model training in accordance with one or more embodiments of the present technology.

In some embodiments, the training system can provide a user interface to collect feedback information from medical personnel. For example, a web application can be provided to the doctors to allow the doctors to highlight important regions in ECG signals. FIGS. 10A-B illustrate example feedback collected for ECG model training using a web interface in accordance with one or more embodiments of the present technology. As shown in FIGS. 10A-B, one or more regions 1005 are marked by the doctor as important regions in the ECG signals. An additional text input field (not shown) can be provided to collect feedback information in the form of natural language explanation. For example, Table 1 shows example textual feedback collected from the doctor for the set of ECG signals (I, II, III, aVR, aVL, aVF, V1-V6).

<center>TABLE 1</center>

<center>Example textual feedback from a doctor</center>

Irregular rhythm with absent P waves and presence of fibrillatory waves throughout the tracing as marked in I, II, III and a VF suggests atrial fibrillation.
Prolonged QRS duration, left axis deviation, qR complex in I and rS complexes in II, II and a VF with increased QRS voltage in limb leads suggests left anterior fascicular block.
Shortened QT interval, characteristic scooped ST depressions in I, II, V4-V6 and increased U wave amplitude suggest digitalis effect.
Inversion of T waves in I, II and flattening in V4-V6 suggests non-specific ischemia.

The highlighted regions and the textual descriptions can be converted to signal importance masks and/or metadata for the training of the neural network engine. The information is then stored in a database and subsequently be retrieved by the model training algorithm.

Figure 11A:
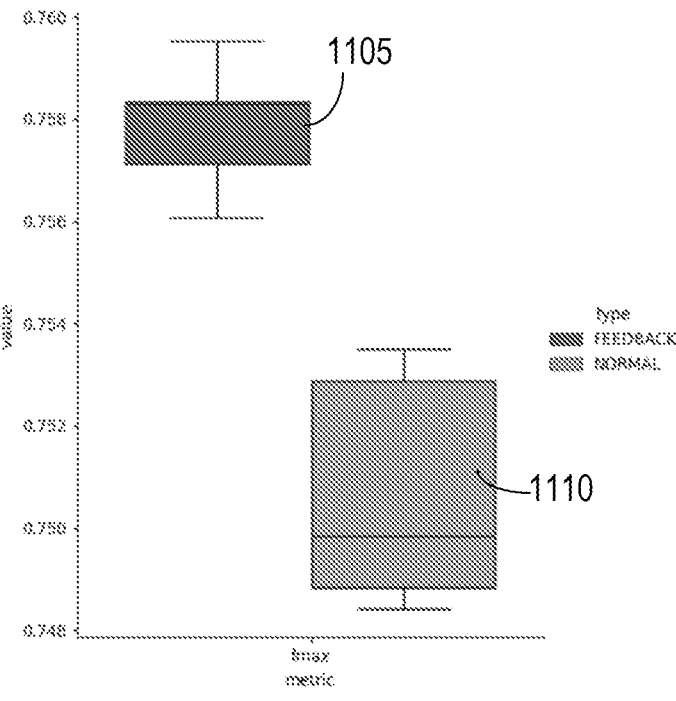
FIG. 11A illustrates an example boxplot for Fmax scores on a test dataset for a normal model and an example model trained with feedback information in accordance with one or more embodiments of the present technology.
Figure 11B:
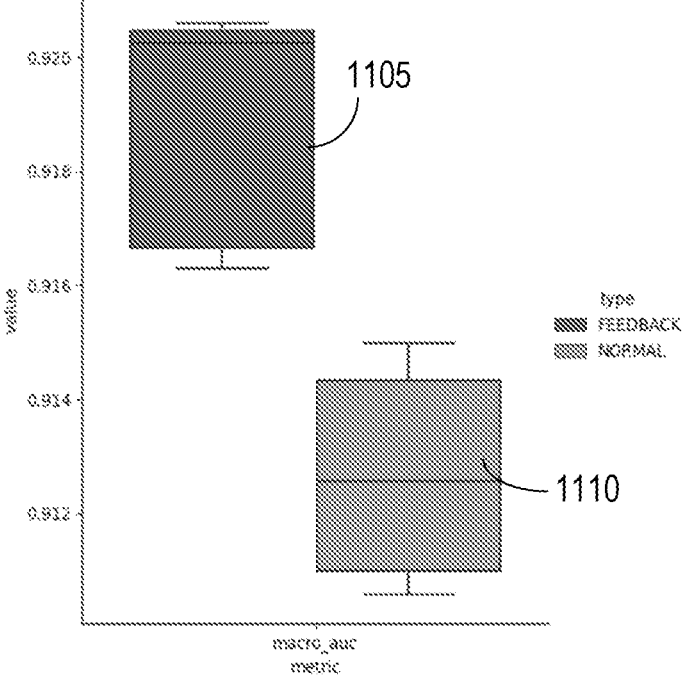
FIG. 11B illustrates an example boxplot macro Area Under receiver operating characteristic Curve (AUC) scores on a test dataset for a normal model and an example model trained with feedback information in accordance with one or more embodiments of the present technology.

FIGS. 11A-B illustrate an example boxplot for Fmax and macro AUC scores on a test dataset for a normal model and an example model trained with feedback information in accordance with one or more embodiments of the present technology. As shown in FIGS. 11A-11B, incorporating the feedback information in training the neural network engine 1105 result in superior performance as compared to a normal neural network engine 1110 trained without any feedback information.

Figure 12A:
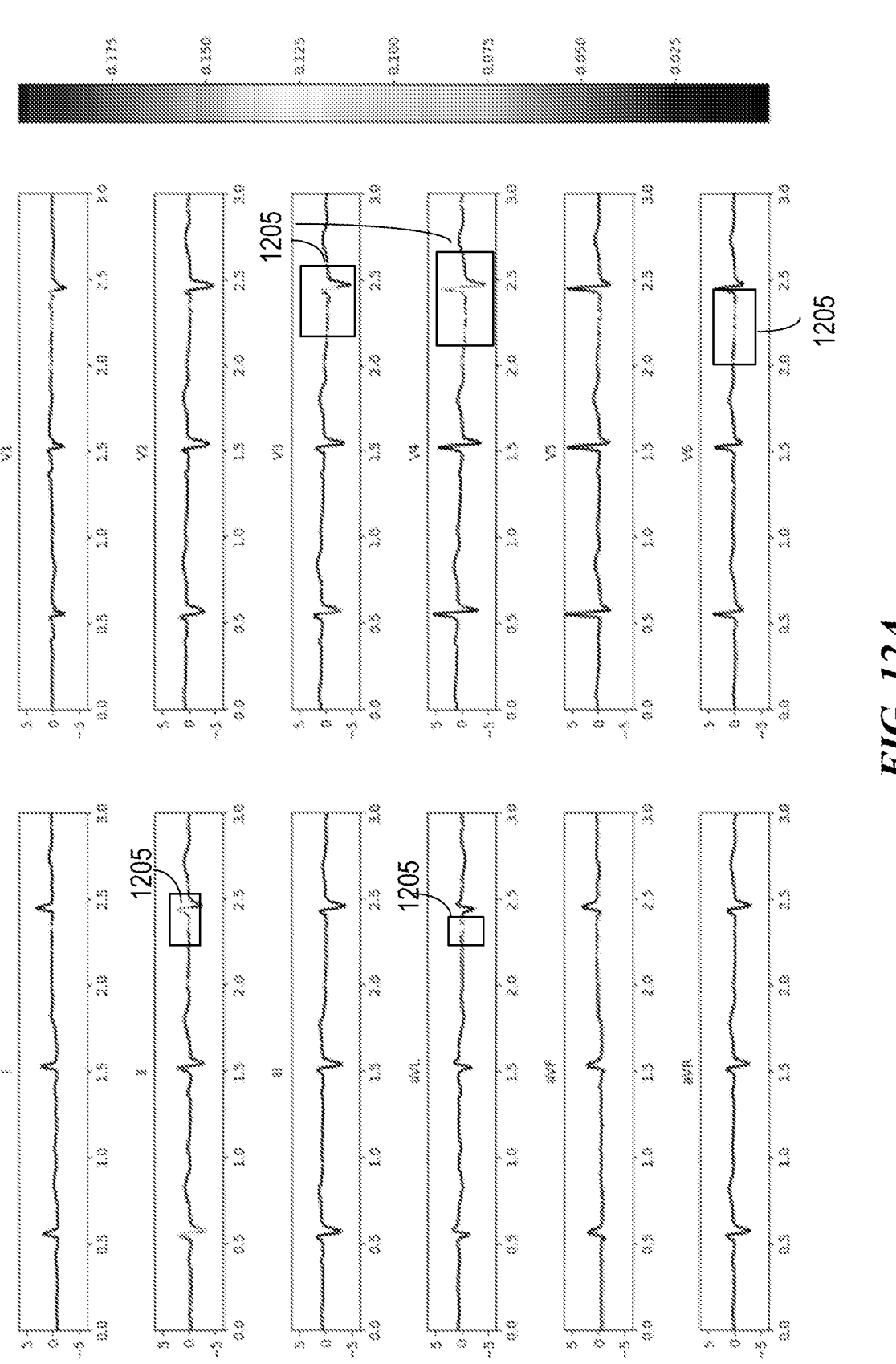
FIG. 12A illustrates an example interpretability map for a normal model.
Figure 12B:
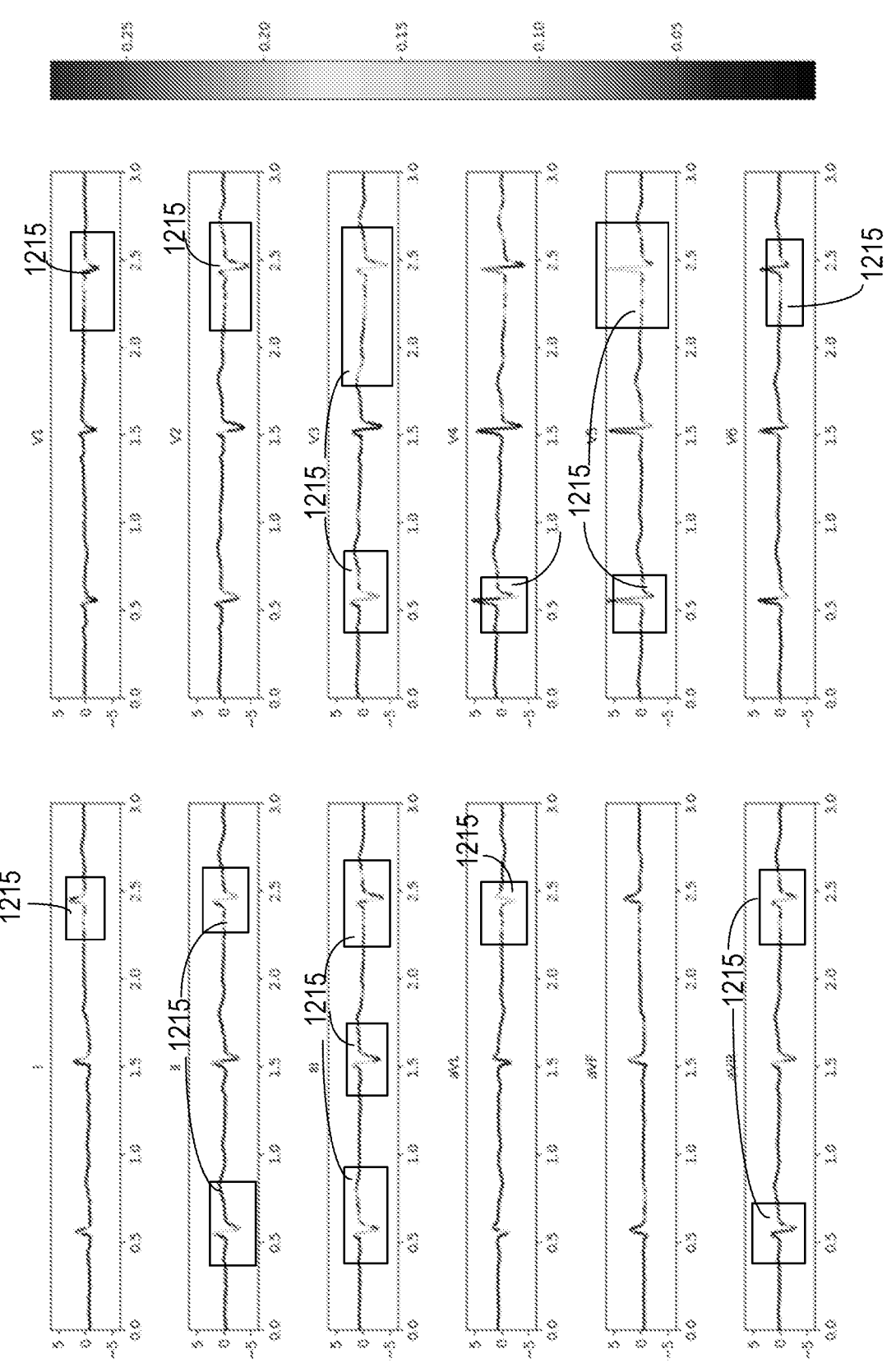
FIG. 12B illustrates an example interpretability map for a model trained with feedback information in accordance with one or more embodiments of the present technology.

FIGS. 12A-B illustrate example interpretability maps for a normal model and an example model trained with feedback information in accordance with one or more embodiments of the present technology. The interpretability maps can be provided to medical practitioners to facilitate the validation and/or annotation process. To generate the interpretability maps, the gradients of the output with respect to the input signals are computed. Regions with large gradients are highlighted as important regions. As shown in FIG. 12A, only a small amount of gradient variations has been detected by the model trained without any feedback information, leading to only a few regions of interest 1205 available for the doctors to review and/or validate. The model trained with feedback information, on the other hand, can accurately identify the gradient variations in the ECG signals and detect the regions of importance 1215 for detecting anomalies. In addition to the graphical depiction of the classification results (e.g., interpretability maps), additional textual information can be included to describe the classification results.

Such information can be provided to the doctors to indicate how the regions are identified by the model, thereby allowing the doctors to validate or correct the classification results without the need to completely re-evaluate the ECG data again. When presented with the example information (e.g., interpretability maps such as shown in FIG. 12B) in a blind study, the medical team has confirmed that the model trained with feedback information can correctly identify regions that normal models fail to detect.

Figure 13:
FIG. 13 is a flowchart representation of a method for performing image classification in accordance with one or more embodiments of the present technology.
Figure 13:
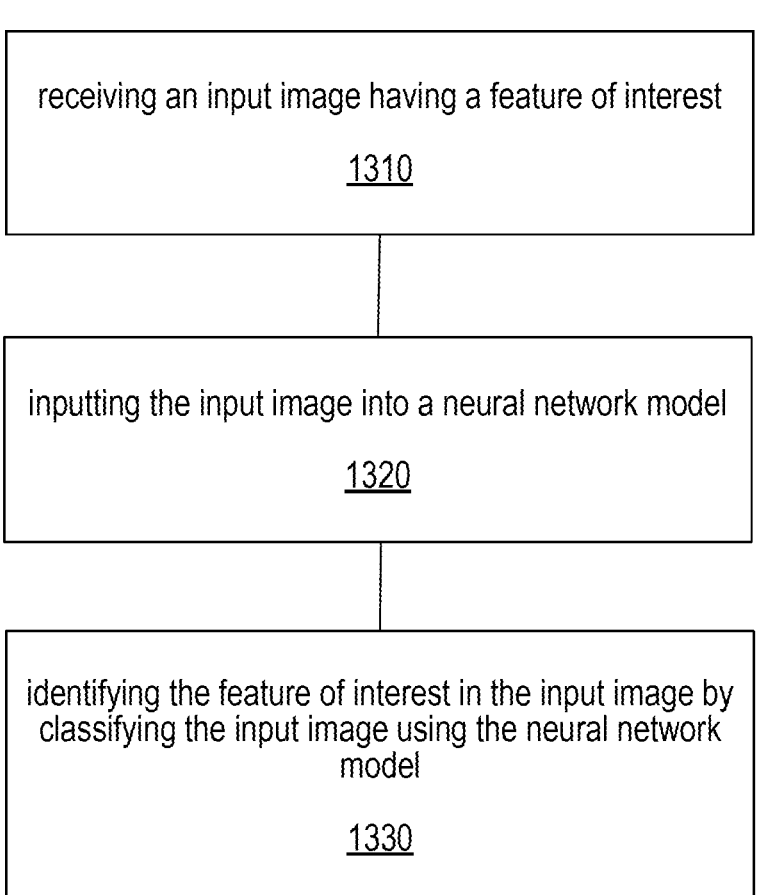

FIG. 13 is a flowchart representation of method for performing image classification in accordance with one or more embodiments of the present technology. The method 1300 includes, at operation 1310, receiving an input image having a feature of interest. The input image is associated with a mask identifying a region that includes the feature of interest. The method includes, at operation 1320, inputting the input image into a neural network model that is trained using an objective function having a first regularization parameter and a second, different regularization parameter. The first regularization parameter indicates a first degree of sensitivity associated with samples located within the mask, and the second regularization parameter indicates a second degree of sensitivity associated with samples located outside of the mask. The method 1300 includes, at operation 1330, identifying the feature of interest in the input image by classifying the input image using the neural network model.

In some embodiments, the method includes receiving feedback information in response to the identified feature. The feedback information is used to validate the identified feature of interest or correct the identified feature. The feedback information is further used to adaptively adjust the neural network engine (e.g., via online training or offline re-training). In some embodiments, the first regularization parameter and the second regularization parameter are greater than zero. In some embodiments, the objective function is based on gradient-based regularization using the first regularization parameter and the second regularization parameter.

Figure 14:
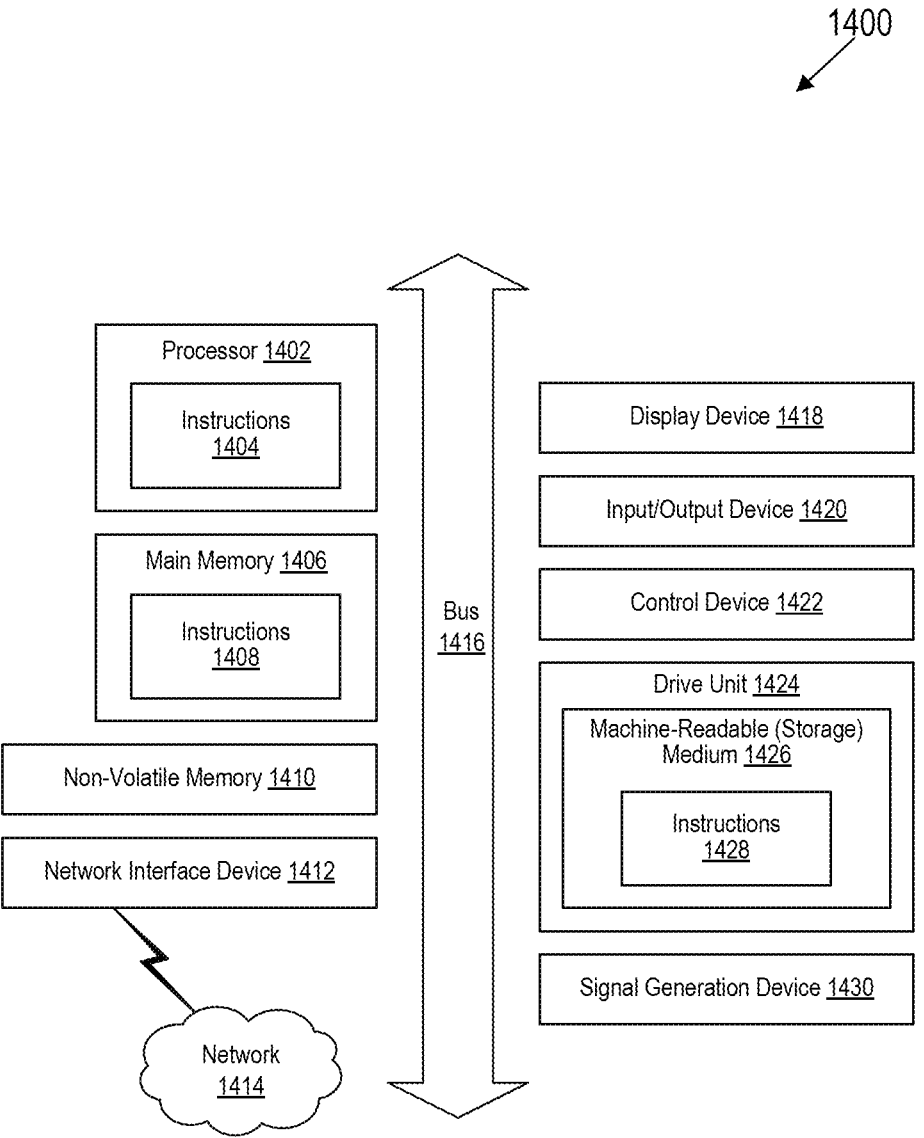
FIG. 14 is a block diagram that illustrates an example of a computer system in which at least some operations described herein can be implemented.

FIG. 14 is a block diagram that illustrates an example of a computer system 1400 in which at least some operations described herein can be implemented. As shown, the computer system 1400 can include: one or more processors 1402, main memory 1406, non-volatile memory 1410, a network interface device 1412, video display device 1418, an input/output device 1420, a control device 1422 (e.g., keyboard and pointing device), a drive unit 1424 that includes a storage medium 1426, and a signal generation device 930 that are communicatively connected to a bus 1416. The bus 1416 represents one or more physical buses and/or point-to-point connections that are connected by appropriate bridges, adapters, or controllers. Various common components (e.g., cache memory) are omitted for brevity. Instead, the computer system 1400 is intended to illustrate a hardware device on which components illustrated or described relative to the examples of the figures and any other components described in this specification can be implemented.

The computer system 1400 can take any suitable physical form. For example, the computing system 1400 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 1400. In some implementation, the computer system 400 can be an embedded computer system, a system-on-chip (SOC), a single-board computer system (SBC) or a distributed system such as a mesh of computer systems or include one or more cloud components in one or more networks. Where appropriate, one or more computer sys- tems 1400 can perform operations in real-time, near real-time, or in batch mode.

The network interface device 1412 enables the computing system 1400 to mediate data in a network 1414 with an entity that is external to the computing system 1400 through any communication protocol supported by the computing system 1400 and the external entity. Examples of the net- work interface device 1412 include a network adaptor card, a wireless network interface card, a router, an access point, a wireless router, a switch, a multilayer switch, a protocol converter, a gateway, a bridge, bridge router, a hub, a digital media receiver, and/or a repeater, as well as all wireless elements noted herein.

The memory (e.g., main memory 1406, non-volatile memory 1410, machine-readable medium 1426) can be local, remote, or distributed. Although shown as a single medium, the machine-readable medium 1426 can include multiple media (e.g., a centralized/distributed database and/ or associated caches and servers) that store one or more sets of instructions 1428. The machine-readable (storage) medium 1426 can include any medium that is capable of storing, encoding, or carrying a set of instructions for execution by the computing system 400. The machine-readable medium 1426 can be non-transitory or comprise a non-transitory device. In this context, a non-transitory stor- age medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-read- able media include recordable-type media such as volatile and non-volatile memory devices 1410, removable flash memory, hard disk drives, optical disks, and transmission-type media such as digital and analog communication links.

In general, the routines executed to implement examples herein can be implemented as part of an operating system or a specific application, component, program, object, module, or sequence of instructions (collectively referred to as "com- puter programs"). The computer programs typically com- prise one or more instructions (e.g., instructions 1404, 1408, 1428) set at various times in various memory and storage devices in computing device(s). When read and executed by the processor 1402, the instruction(s) cause the computing system 1400 to perform operations to execute elements involving the various aspects of the disclosure.

In one example aspect, a system (e.g., the computer system 1400 shown in FIG. 14) for training a neural network engine configured to detect heart anomaly using electrocar- diogram signals is disclosed. The system comprises a pro- cessor that is configured to receive a set of training electro- cardiogram signals. At least one electrocardiogram signal in the set of training electrocardiogram signals is associated with metadata identifying a region of interest that includes a heart anomaly. The processor is configured to input the set of training electrocardiogram signals into the neural network engine. The neural network engine includes an objective function having a first regularization parameter and a second regularization parameter. The first regularization parameter indicates a first degree of sensitivity associated with samples located within the region of interest, and the second regu- larization parameter indicates a second degree of sensitivity associated with samples located outside of the region of interest. The processor is configured to operate the neural network engine to identify the heart anomaly by classifying the set of training electrocardiogram signals and adaptively adjust the neural network engine based on the identified heart anomaly and the metadata.

In some embodiments, the first regularization parameter and the second regularization parameter are different. In some embodiments, the objective function is based on gradient-based regularization using the first regularization parameter and the second regularization parameter. In some embodiments, the processor is configured to adjust the neural network engine by storing the metadata associated with the set of training electrocardiogram signals; and re-training the neural network engine using the stored meta- data and the set of training electrocardiogram signals.

Figure 15:
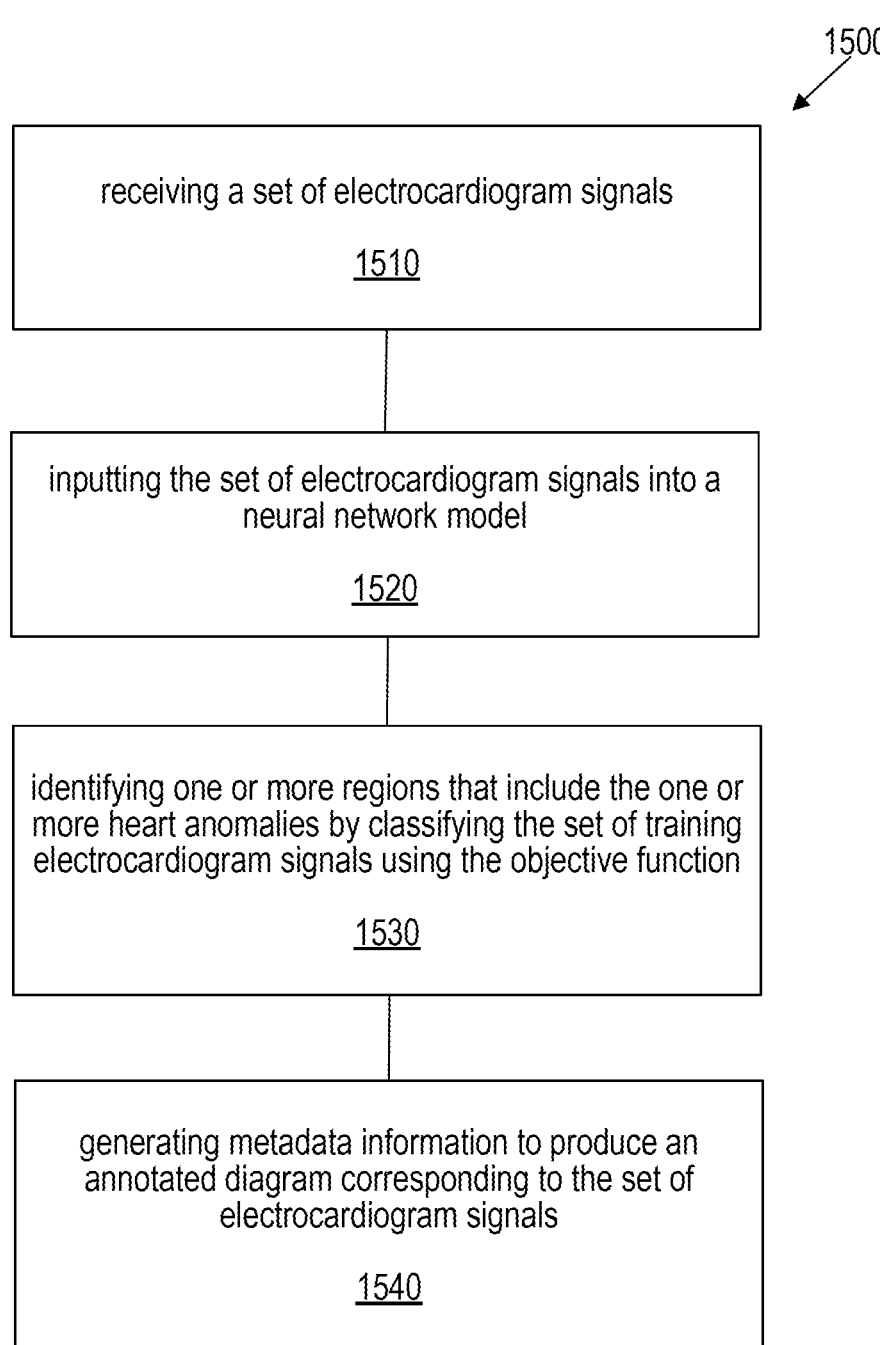
FIG. 15 is a flowchart representation of a method for detecting one or more heart anomalies in accordance with one or more embodiments of the present technology.

In some embodiments, the processor is configured to receive the metadata by querying a database configured to store expert feedback information. In some embodiments, the processor is further configured to provide a user interface to receive the metadata from an expert identifying the region that includes the heart anomaly. In some embodiments, the metadata comprises at least one or more bounding boxes marking boundaries of the region of interest and/or one or more annotations associated with the region of interest that includes the heart anomaly FIG. 15 is a flowchart representation of a method for detecting one or more heart anomalies in electrocardiogram in accordance with one or more embodiments of the present technology. The method 1500 includes, at operation 1510, receiving a set of electrocardiogram signals. The method 1500 includes, at operation 1520, inputting the set of elec- trocardiogram signals into a neural network engine. The neural network engine includes an objective function having a regularization parameter that indicates a degree of sensi- tivity associated with samples located outside of a region of interest. The region of interest is determined based on gradient variation of the set of electrocardiogram signals. The method 1500 includes, at operation 1530, identifying one or more regions that include the one or more heart anomalies by classifying the set of training electrocardio- gram signals using the objective function. The method 1500 also includes, at operation 1540, generating metadata infor- mation to produce an annotated diagram corresponding to the set of electrocardiogram signals. The metadata informa- tion indicates the one or more regions that include the one or more heart anomalies annotated based on the metadata information.

In some embodiments, the method includes providing an interface to receive feedback information in response to the identified one or more heart anomalies, storing the feedback information in a database, and re-training the neural network engine based on at least the feedback information. In some embodiments, the regularization parameter is greater than zero.

In some embodiments, the annotated diagram includes a map generated based on gradient information of the set of electrocardiogram signals determined by the neural network engine. In some embodiments, the annotated diagram includes textual descriptions of the one or more regions that include the one or more heart anomalies. In some embodi- ments, the metadata information indicates how the one or more regions that include the one or more heart anomalies are identified by the neural network engine to enable a medical practitioner to validate or correct the one or more identified regions.

In another example aspect, a system (e.g., the computer system 1400 shown in FIG. 14) for facilitating detection of one or more heart anomalies in electrocardiogram is disclosed. The system includes a processor that is configured to receive information representing a set of electrocardiogram signals, and input the information representing the set of electrocardiogram signals into a neural network engine. The neural network engine is trained using an objective function having a regularization parameter that indicates a degree of sensitivity associated with samples located outside of a region of interest. The region of interest is determined based on gradient variation of the set of electrocardiogram signals. The processor is configured to identify one or more regions that include the one or more heart anomalies by classifying the set of electrocardiogram signals using the neural network engine and generate an annotated diagram corresponding to the set of electrocardiogram signals. The annotated diagram includes metadata information identifying the one or more regions that include the one or more heart anomalies.

In some embodiments, the processor is configured to provide an interface to receive feedback information in response to the identified one or more heart anomalies, store the feedback information in a database, and re-train the neural network engine based on at least the feedback information. In some embodiments, the regularization parameter is greater than zero.

In some embodiments, the annotated diagram includes a map generated based on gradient information of the set of electrocardiogram signals determined by the neural network engine. In some embodiments, the annotated diagram includes textual descriptions of the one or more regions that include the one or more heart anomalies. In some embodiments, the metadata information indicates how the one or more regions that include the one or more heart anomalies are identified by the neural network engine to enable a medical practitioner to validate or correct the one or more identified regions.

It is thus appreciated that the disclosed techniques can be implemented in various neural network engines to provide greater robustness, and interpretability for image classification and ECG anomaly detection.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, e.g., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method for performing classification of image data, the method comprising:

receiving an input image data having a feature of interest, wherein the input image data is associated with a mask identifying a region that includes the feature of interest;

inputting the input image data into a neural network engine that is trained using an objective function having a first regularization parameter and a second regularization parameter different from the first regularization parameter, wherein the first regularization parameter indicates a first degree of sensitivity associated with samples located within the mask, wherein the second regularization parameter indicates a second degree of sensitivity associated with samples located outside of the mask, and wherein the first degree of sensitivity is different from the second degree of sensitivity; and identifying the feature of interest by classifying the input image data using the neural network engine.

2. The method of claim 1, further comprising:

receiving feedback information in response to an identified feature of interest, wherein the feedback information is used to validate the identified feature of interest or correct the identified feature of interest, and wherein the feedback information is used to adjust the neural network engine.

3. The method of claim 2, wherein the neural network engine is adjusted by online training or offline re-training of the neural network engine.

4. The method of claim 1, wherein the first regularization parameter and the second regularization parameter are greater than zero.

5. The method of claim 1, wherein the objective function is based on gradient-based regularization using the first regularization parameter and the second regularization parameter.

* * * * *